US008039209B2

(12) United States Patent
Lindquist et al.

(10) Patent No.: US 8,039,209 B2
(45) Date of Patent: Oct. 18, 2011

(54) YEAST SCREENS FOR TREATMENT OF HUMAN DISEASE

(75) Inventors: Susan Lindquist, Chestnut Hill, MA (US); Sylvia Krobitsch, Berlin (DE); Tiago Fleming Outeiro, Cambridge, MA (US)

(73) Assignee: The University of Chicago, Chicago, IL (US)

( * ) Notice: Subject to any disclaimer, the term of this patent is extended or adjusted under 35 U.S.C. 154(b) by 1106 days.

(21) Appl. No.: 11/363,870

(22) Filed: Feb. 27, 2006

(65) Prior Publication Data

US 2006/0141449 A1  Jun. 29, 2006

Related U.S. Application Data

(62) Division of application No. 10/077,584, filed on Feb. 15, 2002, now Pat. No. 7,045,290.

(60) Provisional application No. 60/269,157, filed on Feb. 15, 2001.

(51) Int. Cl.
*C12Q 1/68* (2006.01)

(52) U.S. Cl. .................. 435/6; 435/254.11; 435/254.21

(58) Field of Classification Search ........................ None
See application file for complete search history.

(56) References Cited

U.S. PATENT DOCUMENTS

| | | | |
|---|---|---|---|
| 5,492,812 | A | 2/1996 | Vooheis |
| 5,547,841 | A | 8/1996 | Marotta et al. |
| 5,643,562 | A | 7/1997 | Kisilevsky et al. |
| 5,652,092 | A | 7/1997 | Vitek et al. |
| 5,686,288 | A | 11/1997 | MacDonald et al. |
| 5,693,757 | A | 12/1997 | MacDonald et al. |
| 5,952,217 | A | 9/1999 | Gorman et al. |
| 5,958,721 | A | 9/1999 | Marshall et al. |
| 5,994,084 | A | 11/1999 | Anderton et al. |
| 6,071,694 | A | 6/2000 | Takashima et al. |
| 6,093,549 | A | 7/2000 | Ross et al. |
| 7,045,290 | B2 | 5/2006 | Lindquist et al. |
| 2001/0006793 | A1 | 7/2001 | Bjornsti et al. |
| 2002/0187157 | A1 | 12/2002 | Jensen et al. |
| 2003/0022243 | A1 | 1/2003 | Kondejewski et al. |
| 2003/0073610 | A1 | 4/2003 | Lindquist et al. |
| 2005/0009019 | A1 | 1/2005 | Van Lueven et al. |
| 2006/0147902 | A1 | 7/2006 | Lindquist et al. |

FOREIGN PATENT DOCUMENTS

| | | |
|---|---|---|
| EP | 1328814 | 10/2006 |
| JP | 2001/501802 | 2/2008 |
| WO | WO 91/04339 | 4/1991 |
| WO | WO 91/05044 | 4/1991 |
| WO | WO 93/03369 | 2/1993 |
| WO | WO 99/06545 | 2/1999 |
| WO | WO 99/29891 | 6/1999 |
| WO | WO 99/62548 | 12/1999 |
| WO | WO 01/02552 | 1/2001 |
| WO | WO 01/06989 | 2/2001 |
| WO | WO 01/23412 | 4/2001 |
| WO | WO 02/35237 | 5/2002 |
| WO | WO 02/065136 | 8/2002 |
| WO | WO 2005/005640 | 1/2005 |

OTHER PUBLICATIONS

Adams et al., "Methods in Yeast Genetics," A Cold Spring Harbor Laboratory Course Manual, 1997.
Borkovich et al,, "hsp82 is an essential protein that is required in higher concentrations for growth of cells at higher temperatures," Mol Cell Biol. 9:3919-3930, 1989.
Boucherie et al., "Differential synthesis of glyceraldehyde-3-phosphate dehydrogenase polypeptides in stressed yeast cells," FEMS Microbiol Lett., 125:127-134, 1995.
Burke et al., "Huntingtin and DRPLA proteins selectively interact with the enzyme GAPDH," Nat Med. 2:347-350, 1996.
Chai et al., "Analysis of the role of heat shock protein (Hsp)molecular chaperones in polyglutamine disease," J Neurosci., 19:10338-10347, 1999.
Chai et al., "Evidence for proteasome involvement in polyglutamine disease: localization to nuclear inclusions in SCA3/MJD and suppression of polyglutamine aggregation in vitro," Hum Mol Genet., 8:673-682, 1999.
Chen and Hochstrasser, "Biogenesis, structure and function of the yeast 20S proteasome," Embo J., 14:2620-2630, 1995.
Cummings et al., "Chaperone suppression of aggregation and altered subcellular proteasome localization imply protein misfolding in SCA1," Nat Genet., 19:148-154, 1998.
DeMarini et al., "The yeast SEN3 gene encodes a regulatory subunit of the 26S proteasome complex required for ubiquitin-dependent protein degradation in vivo," Mol Cell Biol., 15:6311-6321, 1995.
Gething, Guidebook to molecular chaperones and protein folding catalysts. Oxford University Press, 1997.
Jana et al., "Polyglutamine length-dependent interaction of Hsp40 and Hsp70 family chaperones with truncated N-terminal huntingtin: their role in suppression of aggregation and cellular toxicity," Hum Mol Genet., 9(13):2009-2018, 2000.
Kazantsev et al., "Insoluble detergent-resistant aggregates form between pathological and nonpathological lengths of polyglutamine in mammalian cells," Proc Natl Acad Sci U.S.A., 96: 11404-1 1409, 1999.

(Continued)

*Primary Examiner* — James S Ketter

(74) *Attorney, Agent, or Firm* — Fish & Richardson P.C.

(57) ABSTRACT

Screening methods for identifying substances that provide therapeutic value for various diseases associated with protein misfolding are provided. Genetic and chemical screening methods are provided using a yeast system. The methods of the invention provide a rapid and cost-effective method to screen for compounds that prevent protein misfolding and/or protein fibril formation and/or protein aggregation which includes numerous neurodegenerative diseases including Parkinson's disease, Alzheimer's disease, Huntington's disease as well as non-neuronal diseases such as type 2 diabetes.

19 Claims, 4 Drawing Sheets

OTHER PUBLICATIONS

Kimura et al., "Role of the protein chaperone YDJ1 in establishing Hsp90-mediated signal transuction pathways," Science, 268:1362-1365, 1995.

Koo et al., "Amyloid diseases: Abnormal protein aggregation in neurodegeneration," PNAS 96:9989-9990, 1999.

Krobitsch and Lindquist, "Aggregation of huntingtin in yeast varies with the length of the polyglutamine expansion and the expression of chaperone proteins," Proc Natl Acad Sci U.S.A., 97(4):1589-1594, 2000.

Masison et al. "Prion-inducing domain of yeast Ure2p and protease resistance of Ure2p in prion-containing cells," Trends in Genetics, Elsevier Science Publishers, B.V. Amsterdam, NL, 12:14, 1996.

Moore et al., "Triplet repeats form secondary structures that escape DNA repair in yeast," Proc. Natl. Acad. Sci. U.S.A., 96:1504-1509, 1999.

Muchowski et al., "Hsp70 and Hsp40 chaperones can inhibit self-assembly of polyglutamine proteins into amyloid-like fibrils," Proc. Natl. Acad. Sci. USA, 97:7841-7846, 2000.

Mumberg et al., "Regulatable promoters of *Saccharmoyce cerevisiae*: comparison of transcriptional activity and their use for heterologous expression," Nucleic Acids Res. 22:5767-5768, 1994.

Mumberg et al., "Yeast vectors for the controlled expression of heterolgous proteins in different genetic backgrounds," Gene. 156:119-122, 1995.

Nathan and Lindquist, "Mutational analysis of HspPO function: interactions with a steroid receptor and a protein kinase," Mol Cell Biol. 15:3917-3925, 1995.

Nathan et al., "Identification of SSF1, CNS1, and HCH1 as multicopy suppressors of a *Saccharomyces cerevisiae* Hsp90 loss-of-function mutation," Proc. Natl. Acad. Sci. U.S.A. 96:1409-1414, 1999.

Parsell and Lindquist, "The function of heat-shock proteins in stress tolerance: degradation and reactivation of damaged proteins," Annu. Rev. Genet. 27:437-496, 1993.

Parsell et al., "Protein disaggregation mediated by heat-shock protein Hsp104," Nature. 372:475-478, 1994.

Parsell et al., "*Saccharomyces cerevisiae* Hsp104 protein," J. Biol. Chem. 269(6):4480-4487, 1994.

Petko et al., "Hsp26 is not required for growth at high temperatures, nor for thermotolerance, spore development, or germination," Cell., 45:885-894, 1986.

Saudou et al., "Huntingtin acts in the nucleus to induce apoptosis but death does not correlate with the formation of intranuclear inclusions," Cell., 95:55-66, 1998.

Schweitzer et al., "Destabilization of CAG trinucleotide repeat tracts by mismatch repair mutations in yeast," Hum Mol Genet. 6:349-355, 1997.

Stenoien et al., "Polyglutamine-expanded androgen receptors form aggregates that sequester heat shock proteins, proteasome components and SRC-1, and are suppressed by the HDJ-2 chaperone," Hum Mol Genet., 8:731-741, 1999.

Stone and Craig, "Self-regulation of 70-kilodalton heat shock proteins in *Saccharomyces cerevisiae*," Mol Cell Biol., 10:1622-1632, 1990.

Temussi et al., "From Alzheimer's to Huntington: why is a structural understanding so difficult," EMBO Journal 22(3):355-361, 2003.

Tuite et al., "Maintenance and inheritance of yeast prions," Trends in Genetics, Elsevier Science Publishers, B.V. Amsterdam, NL, 12:467-471, 1996.

Vogel et al., "Heat-shock proteins Hsp104 and Hsp70 reactivate mRNA splicing after heat inactivation," Current Biology, 5:306-317, 1995.

Vonsattel et al., "Neuropathological classification of huntington's disease," J Neuropathol Exp Neurol., 44:559-577, 1985.

Neystat et al., "Identification of alpha-synuclein interacting proteins in rat brain by yeast two-hybrid screen," Database Biosis (Online), Biosciences Information Services, XP-002431841, Database Accession No. PREV200100070267, Society for Neuroscience Abstracts, 26:1-2, 2000.

Andoh et al., "Yeast Glycogen Synthase Kinase 3 is Involved in Protein Degradation in Cooperation with Bul1, Bul2, and Rsp5," Moll. Cell. Biol., 20(18):6712-6720 (2000).

Baumann et al., "Abnormal Alzheimer-Like Phosphorylation of Tau-Protein by Cyclin-Dependent Kinases cdk2 and cdk5," FEBS Lett., 336(3):417-424 (1993).

Billingsley et al., "Regulated Phosphorylation and Dephosphorylation of Tau Protein: Effects on Microtubule Interaction, Intracellular Trafficking and Neurodegeneration," Biochem. J., 323:577-591 (1997).

Cafferty, Patrick W., "Characterization of Glycogen Synthase Kinase 3 Beta and Tau Interaction," Dept. of Neurology and Neurosurgery, McGill University (2000).

Cooper et al., "α-Synuclein Blocks ER-Golgi Traffic and Rab1 Rescues Neuron Loss in Parkinson's Models," Science, 313:324-328 (2006).

Crauwels et al., "The Sch9 Protein Kinase in the Yeast *Saccharomyces cerevisiae* Controls cAPK Activity and is Required for Nitrogen Activation of the Fermentable-Growth-Medium-Induced (FGM) Pathway," Microbiology, 143:2627-2637 (1997).

Engelender et al., "Synphilin-1 associates with α-synuclein and promotes the formation of cytosolic inclusions," Nature Genetics, 22:110-114 (1999).

Escher et al., "Taking Yeast from the Brewery to Drug Discovery," Chimia, 54(4):171-173 (2000).

Geyskens et al., "Expression of Mammalian PKB Partially Complements Deletion of the Yeast Protein Kinase Sch9," NATO Science Series, A316:117-126 (2000).

Hartley et al., "The Yak1 Protein Kinase of *Saccharomyces cerevisiae* Moderates Thermotolerance and Inhibits Growth by an Sch9 Protein Kinase-Independent Mechanism," Genetics, 136:465-474 (1994).

Huang et al., "Mammalian Cdk5 is a Functional Homologue of the Budding Yeast Pho85 Cyclin-Dependent Protein Kinase," Proc. Natl. Acad. Sci. USA, 96(25):14445-14450 (1999).

Koo et al., "Amyloid diseases: Abnormal protein aggregation in neurodegeneration," PNAS 96:9989-9990, (1999).

Lindquist, Susan, "Yeast as a Model System for Studying Parkinson's Disease," Grant No. 1R21NS044829-01, (2004) (Abstract Only).

Liu et al., "Oligopeptide-Repeat Expansions Modulate 'Protein-Only' Inheritance in Yeast" Nature 400:573-576 (1999).

Mawal-Dewan et al., "Phosphorylation of Tau Protein by Purified $p34^{cdc28}$ and a Related Protein Kinase from Neurofilaments," J. Biol. Chem., 267(27):19705-19709 (1992).

Notice of Opposition, filed by FoldRx Pharmaceuticals, Inc. against European Patent No. 1373529, Jan. 22, 2009.

Notice of Opposition, filed by ReMYND NV against European Patent No. 1392849, Oct. 2, 2008.

Neystat et al., "Analysis of Synphilin-1 and Synuclein Interactions by Yeast Two-Hybrid β-Galactosidase Liquid Assay," Neuroscience Letters, 325:119-123 (2002).

Ostrerova et al., "α-Synuclein shares physical and functional homology with 14-3-3 proteins," J. Neuroscience, 19(14):5782-5791(1999).

Ostrerova-Golts et al., "The A53T α-Synuclein Mutation Increases Iron-Dependent Aggregation and Toxicity," J. Neuroscience, 20(16):6048-6054 (2000).

Outeiro et al., "Yeast Cells Provide Insight into Alpha-Synuclein Biology and Pathobiology," Science, 302:1772-1775 (2003).

Puziss et al., "MDS1, a Dosage Suppressor of an *mck1*Mutant, Encodes a Putative Yeast Homolog of Glycogen Synthase Kinase 3," Molecular and Cellular Biology, 14:831-839 (1994).

Song et al., "Proteolytic Processing and Degradation of Human Presenilin-1 Expressed in Yeast," Neuroscience Letters, 282:65-68 (2000).

Spillantini MG et al., "Endogenous Proviruses as 'memento's',"Nature, 388:839-840, (1997).

Tanaka et al., "Inducible Expression of Mutant α-Synuclein Decreases Proteasome Activity and Increases Sensitivity to Mitochondria-Dependent Apoptosis," Human Molecular Genetics, 10(9):919-926 (2001).

Temussi et al., "From Alzheimer's to Huntington: why is a structural understanding so difficult," EMBO Journal 22(3):355-361, (2003).

Thevelein, J.M.,"Signal Transduction in Yeast," Yeast, 10:1753-1790 (1994).

Tuite et al., "Maintenance and Inheritance of Yeast Prions," *Trends in Genetics*, Elsevier Science Publishers, 12(11):467-471 (1996).

Willingham et al., "Yeast Genes that Enhance the Toxicity of a Mutant Huntingtin Fragment or α-Synuclein," *Science*, 302:1769-1772 (2003).

Woods et al., "The Kinase DYRK Phosphorylates Protein-Synthesis Initiation Factor eIF2Bε at Ser$^{539}$ and the Microtubule-Associated Protein tau at Thr$^{212}$: Potential Role for DYRK as a Glycogen Synthase Kinase 3-Priming Kinase," Biochem. J., 355:609-615 (2001).

Yamaguchi et al., "Preferential Labeling of Alzheimer Neurofibrillary Tangles with Antisera for Tau Protein Kinase (TPK) I/Glycogen Synthase Kinase-3ε and Cyclin-Dependent Kinase 5, a component of TPK II," *Acta Neuropathol.*, 92:232-241 (1996).

Yan et al., "Membrane Receptors, Sensors and Transporters," *Yeast*, 18(S1):S273 (2001).

Zhang et al., "Interaction of the E1A Oncoprotein with Yak1p, a Novel Regulator of Yeast Pseudohyphal Differentiation, and Related Mammalian Kinases," *Molecular Biology of the Cell*, 12:699-710 (2001).

Zhou et al., "Pin1-Dependent Prolyl Isomerization Regulates Dephosphorylation of Cdc25C and Tau Proteins," *Molecular Cell*, 6:873-883 (2000).

Kilmartin et al., "Structural Rearrangements of Tubulin and Actin During the Cell Cycle of the Yeast *Saccharomyces*," *J. Cell Biol.*, 98:922-933 (1984).

Pringle et al., "Staining of Bud Scars and Other Cell Wall Chitin with Calcofluor," *J. Meth. Enzym.*, 194:732-732 (1981).

Proprietor's Observations to the European Patent Office on the Opposition filed by ReMynd NV against EP 1392849 B1, dated Jun. 25, 2009.

Proprietor's Observations to the European Patent Office on the Opposition filed by FoldRx against EP 1373529 B1, dated Sep. 2, 2009.

Richardson et al., "Mouse Models of Alzheimer's Disease: A Quest for Plaques and Tangles," *ILAR Journal*, 43:89-99 (2002).

European Patent Office, Summons to attend Oral Proceedings pursuant to Rule 115 (1) EPC, dated Apr. 29, 2010 (14 pages).

Proprietor's Observations Pursuant to Rule 116 EPC in Preparation for Oral Proceedings on Nov. 2, 2010 to the European Patent Office on the Opposition filed by ReMynd NV against EP 1392849, dated Aug. 31, 2010 (16 pages).

Letter from the Opponent (ReMynd NV) in Preparation for Oral Proceedings on Nov. 2, 2010 to the European Patent Office on the Opposition filed against EP 1392849, dated Sep. 2, 2010 (13 pages).

European Patent Office, Communication from the European Patent Office regarding the claims allowed after completion of the Opposition filed against EP 1392849, dated Nov. 4, 2010 (11 pages).

European Patent Office, Interlocutory Decision of the Opposition Division dated Jan. 14, 2011 issued in connection with the Oral Proceeding of Nov. 2, 2010 in counterpart European Patent Application No. 02718994.3-1223/1392849, 76 pages.

European Patent Office, Preliminary Opinion (Summary of Facts and Submissions) in European Patent Application No. 02 702 181.5, dated May 11, 2011 (8 pages).

Sis1p deletions/truncations

Q 25-

SEQUENCE LISTING

```
<160> NUMBER OF SEQ ID NOS: 9

<210> SEQ ID NO 1
<211> LENGTH: 423
<212> TYPE: DNA
<213> ORGANISM: Homo sapiens
<220> FEATURE:
<221> NAME/KEY: CDS
<222> LOCATION: (1)..(414)

<400> SEQUENCE: 1 atg gat gta ttc atg aaa gga ctt tca aag gcc aag gag gga gtt gtg         48
Met Asp Val Phe Met Lys Gly Leu Ser Lys Ala Lys Glu Gly Val Val
  1               5                  10                  15 gct gct gct gag aaa acc aaa cag ggt gtg gca gaa gca gca gga aag         96
Ala Ala Ala Glu Lys Thr Lys Gln Gly Val Ala Glu Ala Ala Gly Lys
             20                  25                  30 aca aaa gag ggt gtt ctc tat gta ggc tcc aaa acc aag gag gga gtg        144
Thr Lys Glu Gly Val Leu Tyr Val Gly Ser Lys Thr Lys Glu Gly Val
         35                  40                  45 gtg cat ggt gtg gca aca gtg gct gag aag acc aaa gag caa gtg aca        192
Val His Gly Val Ala Thr Val Ala Glu Lys Thr Lys Glu Gln Val Thr
     50                  55                  60 aat gtt gga gga gca gtg gtg acg ggt gtg aca gca gta gcc cag aag        240
Asn Val Gly Gly Ala Val Val Thr Gly Val Thr Ala Val Ala Gln Lys
 65                  70                  75                  80 aca gtg gag gga gca ggg agc att gca gca gcc act ggc ttt gtc aaa        288
Thr Val Glu Gly Ala Gly Ser Ile Ala Ala Ala Thr Gly Phe Val Lys
                 85                  90                  95 aag gac cag ttg ggc aag aat gaa gaa gga gcc cca cag gaa gga att        336
Lys Asp Gln Leu Gly Lys Asn Glu Glu Gly Ala Pro Gln Glu Gly Ile
            100                 105                 110 ctg gaa gat atg cct gtg gat cct gac aat gag gct tat gaa atg cct        384
Leu Glu Asp Met Pro Val Asp Pro Asp Asn Glu Ala Tyr Glu Met Pro
        115                 120                 125 tct gag gaa ggg tat caa gac tac gaa cct gaagcctaa                      423
Ser Glu Glu Gly Tyr Gln Asp Tyr Glu Pro
    130                 135

<210> SEQ ID NO 2
<211> LENGTH: 138
<212> TYPE: PRT
<213> ORGANISM: Homo sapiens

<400> SEQUENCE: 2

Met Asp Val Phe Met Lys Gly Leu Ser Lys Ala Lys Glu Gly Val Val
  1               5                  10                  15

Ala Ala Ala Glu Lys Thr Lys Gln Gly Val Ala Glu Ala Ala Gly Lys
             20                  25                  30

Thr Lys Glu Gly Val Leu Tyr Val Gly Ser Lys Thr Lys Glu Gly Val
         35                  40                  45
```

```
Val His Gly Val Ala Thr Val Ala Glu Lys Thr Lys Glu Gln Val Thr
     50                  55                  60
Asn Val Gly Gly Ala Val Val Thr Gly Val Thr Ala Val Ala Gln Lys
 65                  70                  75                  80
Thr Val Glu Gly Ala Gly Ser Ile Ala Ala Ala Thr Gly Phe Val Lys
                 85                  90                  95
Lys Asp Gln Leu Gly Lys Asn Glu Glu Gly Ala Pro Gln Glu Gly Ile
                100                 105                 110
Leu Glu Asp Met Pro Val Asp Pro Asp Asn Glu Ala Tyr Glu Met Pro
            115                 120                 125
Ser Glu Glu Gly Tyr Gln Asp Tyr Glu Pro
        130                 135

<210> SEQ ID NO 3
<211> LENGTH: 1236
<212> TYPE: DNA
<213> ORGANISM: Homo sapiens
<220> FEATURE:
<221> NAME/KEY: CDS
<222> LOCATION: (1)..(513)

<400> SEQUENCE: 3 atg gcg acc ctg gaa aag ctg atg aag gcc ttc gag tcc ctc aaa agc    48
Met Ala Thr Leu Glu Lys Leu Met Lys Ala Phe Glu Ser Leu Lys Ser
 1               5                  10                  15 ttc caa cag cag caa cag caa caa cag cag caa cag caa caa cag cag    96
Phe Gln Gln Gln Gln Gln Gln Gln Gln Gln Gln Gln Gln Gln Gln Gln
             20                  25                  30 caa cag caa caa cag cag caa cag caa caa cag cag caa cag caa caa   144
Gln Gln Gln Gln Gln Gln Gln Gln Gln Gln Gln Gln Gln Gln Gln Gln
         35                  40                  45 cag cag caa cag caa caa cag cag caa cag caa caa cag cag caa cag   192
Gln Gln Gln Gln Gln Gln Gln Gln Gln Gln Gln Gln Gln Gln Gln Gln
     50                  55                  60 caa caa cag cag caa cag caa caa cag cag caa cag caa caa cag cag   240
Gln Gln Gln Gln Gln Gln Gln Gln Gln Gln Gln Gln Gln Gln Gln Gln
 65                  70                  75                  80 caa cag caa caa cag cag caa cag caa caa cag cag caa cag caa caa   288
Gln Gln Gln Gln Gln Gln Gln Gln Gln Gln Gln Gln Gln Gln Gln Gln
                 85                  90                  95 cag cag caa cag caa caa cag cag caa cag caa caa cag cag caa cag   336
Gln Gln Gln Gln Gln Gln Gln Gln Gln Gln Gln Gln Gln Gln Gln Gln
                100                 105                 110 caa caa cag cag caa cag caa caa ccg cca cca cct ccc cct cca ccc   384
Gln Gln Gln Gln Gln Gln Gln Gln Pro Pro Pro Pro Pro Pro Pro Pro
            115                 120                 125 cca cct cct caa ctt cct caa cct cct cca cag gca cag cct ctg ctg   432
Pro Pro Pro Gln Leu Pro Gln Pro Pro Pro Gln Ala Gln Pro Leu Leu
        130                 135                 140 cct cag cca caa cct cct cca cct cca cct cca cct cct cca ggc cca   480
Pro Gln Pro Gln Pro Pro Pro Pro Pro Pro Pro Pro Pro Pro Gly Pro
145                 150                 155                 160 gct gtg gct gag gag cct ctg cac cga cct gga tccctggtga gcaagggcga  533
Ala Val Ala Glu Glu Pro Leu His Arg Pro Gly
            165                 170 ggagctgttc accggggtgg tgcccatcct ggtcgagctg gacggcgacg taaacggcca   593
caagttcagc gtgtccggcg agggcgaggg cgatgccacc tacggcaagc tgaccctgaa   653
gttcatctgc accaccggca agctgcccgt gccctggccc accctcgtga ccaccctgac   713
```

-continued

```
ctacggcgtg cagtgcttca gccgctaccc cgaccacatg aagcagcacg acttcttcaa      773
gtccgccatg cccgaaggct acgtccagga gcgcaccatc ttcttcaagg acgacggcaa      833
ctacaagacc cgcgccgagg tgaagttcga gggcgacacc ctggtgaacc gcatcgagct      893
gaagggcatc gacttcaagg aggacggcaa catcctgggg cacaagctgg agtacaacta      953
caacagccac aacgtctata tcatggccga caagcagaag aacggcatca aggtgaactt     1013
caagatccgc cacaacatcg aggacggcag cgtgcagctc gccgaccact accagcagaa     1073
cacccccatc ggcgacggcc ccgtgctgct gcccgacaac cactacctga gcacccagtc     1133
cgccctgagc aaagacccca acgagaagcg cgatcacatg gtcctgctgg agttcgtgac     1193
cgccgccggg atcactctcg gcatggacga gctgtacaag taa                       1236
```

<210> SEQ ID NO 4
<211> LENGTH: 171
<212> TYPE: PRT
<213> ORGANISM: Homo sapiens

<400> SEQUENCE: 4

```
Met Ala Thr Leu Glu Lys Leu Met Lys Ala Phe Glu Ser Leu Lys Ser
  1               5                  10                  15

Phe Gln Gln Gln Gln Gln Gln Gln Gln Gln Gln Gln Gln Gln Gln Gln
                 20                  25                  30

Gln Gln Gln Gln Gln Gln Gln Gln Gln Gln Gln Gln Gln Gln Gln Gln
             35                  40                  45

Gln Gln Gln Gln Gln Gln Gln Gln Gln Gln Gln Gln Gln Gln Gln Gln
         50                  55                  60

Gln Gln Gln Gln Gln Gln Gln Gln Gln Gln Gln Gln Gln Gln Gln Gln
 65                  70                  75                  80

Gln Gln Gln Gln Gln Gln Gln Gln Gln Gln Gln Gln Gln Gln Gln Gln
                 85                  90                  95

Gln Gln Gln Gln Gln Gln Gln Gln Gln Gln Gln Gln Gln Gln Gln Gln
            100                 105                 110

Gln Gln Gln Gln Gln Gln Gln Gln Pro Pro Pro Pro Pro Pro Pro Pro
        115                 120                 125

Pro Pro Pro Gln Leu Pro Gln Pro Pro Pro Gln Ala Gln Pro Leu Leu
    130                 135                 140

Pro Gln Pro Gln Pro Pro Pro Pro Pro Pro Pro Pro Pro Gly Pro
145                 150                 155                 160

Ala Val Ala Glu Glu Pro Leu His Arg Pro Gly
                165                 170
```

<210> SEQ ID NO 5
<211> LENGTH: 1002
<212> TYPE: DNA
<213> ORGANISM: Homo sapiens
<220> FEATURE:
<221> NAME/KEY: CDS
<222> LOCATION: (1)..(189)

<400> SEQUENCE: 5

```
atg gcg acc ctg gaa aag ctg atg aag gcc ttc gag tcc ctc aaa agc        48
Met Ala Thr Leu Glu Lys Leu Met Lys Ala Phe Glu Ser Leu Lys Ser
  1               5                  10                  15 ttc caa cag cag caa cag caa caa cag cag caa cag caa caa cag cag        96
Phe Gln Gln Gln Gln Gln Gln Gln Gln Gln Gln Gln Gln Gln Gln Gln
                 20                  25                  30 caa cag caa caa cag cag caa cag caa caa ccg cca cca cct ccc cct       144
Gln Gln Gln Gln Gln Gln Gln Gln Gln Gln Pro Pro Pro Pro Pro Pro
```

|  |  |
|---|---|
| cca ccc cca cct cct caa ctt cct caa cct cct cca cag gca cag<br>Pro Pro Pro Pro Pro Gln Leu Pro Gln Pro Pro Gln Ala Gln<br>     50                    55                  60 | 189 |
| cctctgctgc ctcagccaca acctcctcca cctccacctc cacctcctcc aggcccagct | 249 |
| gtggctgagg agcctctgca ccgacctgga tccctggtga gcaagggcga ggagctgttc | 309 |
| accggggtgg tgcccatcct ggtcgagctg gacggcgacg taaacggcca aagttcagc | 369 |
| gtgtccggcg agggcgaggg cgatgccacc tacggcaagc tgaccctgaa gttcatctgc | 429 |
| accaccggca agctgcccgt gccctggccc accctcgtga ccaccctgac ctacggcgtg | 489 |
| cagtgcttca gccgctaccc cgaccacatg aagcagcacg acttcttcaa gtccgccatg | 549 |
| cccgaaggct acgtccagga gcgcaccatc ttcttcaagg acgacggcaa ctacaagacc | 609 |
| cgcgccgagg tgaagttcga gggcgacacc ctggtgaacc gcatcgagct gaagggcatc | 669 |
| gacttcaagg aggacggcaa catcctgggg cacaagctgg agtacaacta caacagccac | 729 |
| aacgtctata tcatggccga caagcagaag aacggcatca aggtgaactt caagatccgc | 789 |
| cacaacatcg aggacggcag cgtgcagctc gccgaccact accagcagaa cacccccatc | 849 |
| ggcgacggcc ccgtgctgct gcccgacaac cactacctga gcacccagtc cgccctgagc | 909 |
| aaagacccca acgagaagcg cgatcacatg gtcctgctgg agttcgtgac cgccgccggg | 969 |
| atcactctcg gcatggacga gctgtacaag taa | 1002 |

<210> SEQ ID NO 6
<211> LENGTH: 63
<212> TYPE: PRT
<213> ORGANISM: Homo sapiens

<400> SEQUENCE: 6

Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln
            20                  25                  30

Gln Gln Gln Gln Gln Gln Gln Gln Gln Pro Pro Pro Pro Pro
        35                  40                  45

Pro Pro Pro Pro Pro Gln Leu Pro Gln Pro Pro Pro Gln Ala Gln
    50                  55                  60

<210> SEQ ID NO 7
<211> LENGTH: 1059
<212> TYPE: DNA
<213> ORGANISM: Saccharomyces cerevisiae
<220> FEATURE:
<221> NAME/KEY: CDS
<222> LOCATION: (1)..(1056)

<400> SEQUENCE: 7

|  |  |
|---|---|
| atg gtc aag gag aca aaa ctt tat gat tta ctt gga gta tct cca agt<br>Met Val Lys Glu Thr Lys Leu Tyr Asp Leu Leu Gly Val Ser Pro Ser<br>1               5                 10                15 | 48 |
| gct aat gag caa gaa ctg aaa aag ggt tat aga aaa gca gct cta aaa<br>Ala Asn Glu Gln Glu Leu Lys Lys Gly Tyr Arg Lys Ala Ala Leu Lys<br>          20                    25                    30 | 96 |
| tat cat cca gat aag cca aca ggt gac aca gaa aag ttt aag gag ata<br>Tyr His Pro Asp Lys Pro Thr Gly Asp Thr Glu Lys Phe Lys Glu Ile<br>        35                    40                    45 | 144 |
| tca gag gcc ttt gaa att tta aat gat cct caa aaa agg gaa ata tat<br>Ser Glu Ala Phe Glu Ile Leu Asn Asp Pro Gln Lys Arg Glu Ile Tyr<br>    50                    55                    60 | 192 |

```
gat caa tac ggt ctc gag gct gct aga tct ggt ggt cca agc ttt ggt    240
Asp Gln Tyr Gly Leu Glu Ala Ala Arg Ser Gly Gly Pro Ser Phe Gly
 65                  70                  75                  80 cct ggt ggt cct ggc ggt gct gga ggt gct gga ggc ttc cct ggc ggt    288
Pro Gly Gly Pro Gly Gly Ala Gly Gly Ala Gly Gly Phe Pro Gly Gly
                 85                  90                  95 gcg ggc gga ttc tcc gga gga cat gcg ttc agt aat gag gat gct ttc    336
Ala Gly Gly Phe Ser Gly Gly His Ala Phe Ser Asn Glu Asp Ala Phe
            100                 105                 110 aat att ttt tca caa ttc ttt ggc ggc agt tcc cca ttc ggt ggt gct    384
Asn Ile Phe Ser Gln Phe Phe Gly Gly Ser Ser Pro Phe Gly Gly Ala
        115                 120                 125 gat gac agt ggc ttc agt ttc tct agt tat cca tct ggc ggt ggt gct    432
Asp Asp Ser Gly Phe Ser Phe Ser Ser Tyr Pro Ser Gly Gly Gly Ala
    130                 135                 140 ggt atg gga ggt atg cct gga gga atg gga gga atg cat ggc ggc atg    480
Gly Met Gly Gly Met Pro Gly Gly Met Gly Gly Met His Gly Gly Met
145                 150                 155                 160 gga ggt atg cct ggc ggc ttt aga tca gca tca agc tct ccc acg tat    528
Gly Gly Met Pro Gly Gly Phe Arg Ser Ala Ser Ser Ser Pro Thr Tyr
                165                 170                 175 cca gag gaa gaa aca gtt caa gtt aat tta cca gtt agt cta gaa gat    576
Pro Glu Glu Glu Thr Val Gln Val Asn Leu Pro Val Ser Leu Glu Asp
            180                 185                 190 ttg ttt gtt ggt aaa aag aag tca ttt aaa att gga aga aag ggc cca    624
Leu Phe Val Gly Lys Lys Lys Ser Phe Lys Ile Gly Arg Lys Gly Pro
        195                 200                 205 cat ggg gcc tct gaa aag aca caa att gac att caa tta aaa ccg ggt    672
His Gly Ala Ser Glu Lys Thr Gln Ile Asp Ile Gln Leu Lys Pro Gly
    210                 215                 220 tgg aaa gct ggt acc aaa ata aca tac aag aac cag ggt gat tac aat    720
Trp Lys Ala Gly Thr Lys Ile Thr Tyr Lys Asn Gln Gly Asp Tyr Asn
225                 230                 235                 240 cct caa acg ggc cgt aga aag act ttg cag ttt gtc atc cag gaa aag    768
Pro Gln Thr Gly Arg Arg Lys Thr Leu Gln Phe Val Ile Gln Glu Lys
                245                 250                 255 agc cat cca aac ttt aaa aga gac ggt gat gac cta att tac act ctg    816
Ser His Pro Asn Phe Lys Arg Asp Gly Asp Asp Leu Ile Tyr Thr Leu
            260                 265                 270 cca cta tct ttc aag gaa tca ttg tta ggt ttt tca aaa act atc caa    864
Pro Leu Ser Phe Lys Glu Ser Leu Leu Gly Phe Ser Lys Thr Ile Gln
        275                 280                 285 aca att gat ggc aga acc tta cct ttg tcg aga gta cag cct gtc caa    912
Thr Ile Asp Gly Arg Thr Leu Pro Leu Ser Arg Val Gln Pro Val Gln
    290                 295                 300 ccc tca caa act tct act tat cct ggt caa ggt atg cca act cca aag    960
Pro Ser Gln Thr Ser Thr Tyr Pro Gly Gln Gly Met Pro Thr Pro Lys
305                 310                 315                 320 aac cca tct cag aga ggt aat ttg att gta aaa tat aaa gtg gac tat   1008
Asn Pro Ser Gln Arg Gly Asn Leu Ile Val Lys Tyr Lys Val Asp Tyr
                325                 330                 335 cca ata tca cta aac gac gct caa aaa cgt gct ata gat gaa aat ttt   1056
Pro Ile Ser Leu Asn Asp Ala Gln Lys Arg Ala Ile Asp Glu Asn Phe
            340                 345                 350 taa                                                               1059

<210> SEQ ID NO 8
<211> LENGTH: 352
<212> TYPE: PRT
<213> ORGANISM: Saccharomyces cerevisiae
```

-continued

<400> SEQUENCE: 8

Met Val Lys Glu Thr Lys Leu Tyr Asp Leu Gly Val Ser Pro Ser
1               5                   10                  15

Ala Asn Glu Gln Glu Leu Lys Lys Gly Tyr Arg Lys Ala Ala Leu Lys
            20                  25                  30

Tyr His Pro Asp Lys Pro Thr Gly Asp Thr Glu Lys Phe Lys Glu Ile
        35                  40                  45

Ser Glu Ala Phe Glu Ile Leu Asn Asp Pro Gln Lys Arg Glu Ile Tyr
    50                  55                  60

Asp Gln Tyr Gly Leu Glu Ala Ala Arg Ser Gly Gly Pro Ser Phe Gly
65                  70                  75                  80

Pro Gly Gly Pro Gly Gly Ala Gly Gly Ala Gly Gly Phe Pro Gly Gly
                85                  90                  95

Ala Gly Gly Phe Ser Gly Gly His Ala Phe Ser Asn Glu Asp Ala Phe
            100                 105                 110

Asn Ile Phe Ser Gln Phe Phe Gly Gly Ser Ser Pro Phe Gly Gly Ala
        115                 120                 125

Asp Asp Ser Gly Phe Ser Phe Ser Ser Tyr Pro Ser Gly Gly Gly Ala
    130                 135                 140

Gly Met Gly Gly Met Pro Gly Gly Met Gly Gly Met His Gly Gly Met
145                 150                 155                 160

Gly Gly Met Pro Gly Gly Phe Arg Ser Ala Ser Ser Pro Thr Tyr
                165                 170                 175

Pro Glu Glu Glu Thr Val Gln Val Asn Leu Pro Val Ser Leu Glu Asp
            180                 185                 190

Leu Phe Val Gly Lys Lys Lys Ser Phe Lys Ile Gly Arg Lys Gly Pro
        195                 200                 205

His Gly Ala Ser Glu Lys Thr Gln Ile Asp Ile Gln Leu Lys Pro Gly
    210                 215                 220

Trp Lys Ala Gly Thr Lys Ile Thr Tyr Lys Asn Gln Gly Asp Tyr Asn
225                 230                 235                 240

Pro Gln Thr Gly Arg Arg Lys Thr Leu Gln Phe Val Ile Gln Glu Lys
                245                 250                 255

Ser His Pro Asn Phe Lys Arg Asp Gly Asp Asp Leu Ile Tyr Thr Leu
            260                 265                 270

Pro Leu Ser Phe Lys Glu Ser Leu Leu Gly Phe Ser Lys Thr Ile Gln
        275                 280                 285

Thr Ile Asp Gly Arg Thr Leu Pro Leu Ser Arg Val Gln Pro Val Gln
    290                 295                 300

Pro Ser Gln Thr Ser Thr Tyr Pro Gly Gln Gly Met Pro Thr Pro Lys
305                 310                 315                 320

Asn Pro Ser Gln Arg Gly Asn Leu Ile Val Lys Tyr Lys Val Asp Tyr
                325                 330                 335

Pro Ile Ser Leu Asn Asp Ala Gln Lys Arg Ala Ile Asp Glu Asn Phe
            340                 345                 350

<210> SEQ ID NO 9
<211> LENGTH: 68
<212> TYPE: PRT
<213> ORGANISM: Homo sapiens

<400> SEQUENCE: 9

Met Ala Thr Leu Glu Lys Leu Met Lys Ala Phe Glu Ser Leu Lys Ser
1               5                   10                  15

```
Phe Pro Pro Pro Pro Pro Pro Pro Pro Pro Pro Gln Leu Pro Gln
            20                  25              30

Pro Pro Pro Gln Ala Gln Pro Leu Leu Pro Gln Pro Gln Pro Pro Pro
        35                  40              45

Pro Pro Pro Pro Pro Pro Gly Pro Ala Val Ala Glu Glu Pro Leu
    50              55              60

His Arg Pro Gly
65
```

YEAST SCREENS FOR TREATMENT OF HUMAN DISEASE

This application is a divisional of U.S. application Ser. No. 10/077,584, filed Feb. 15, 2002 now U.S. Pat. No. 7,045,290, which claims priority to U.S. Provisional Patent Application No. 60/269,157 filed on Feb. 15, 2001, which are incorporated by reference in their entirety herein.

The government may own rights in the present invention pursuant to grant number R37GM25874 from the National Institutes of Health. Funding from the Howard Hughes Medical Institute is also acknowledged.

BACKGROUND OF THE INVENTION

1. Field of the Invention

The present invention relates generally to the fields of genetic and chemical screening and diseases associated with protein misfolding. More particularly, it concerns the development of a yeast-based system that can be used to screen for substances that provide therapeutic value for various diseases associated with protein misfolding. Methods for performing genetic and chemical screens using the yeast systems of the invention are also provided. One major class of diseases benefited by the methods of the invention are the neurodegenerative diseases including Parkinson's disease, Alzheimer's disease, Huntington's disease and the like.

2. Description of Related Art

The correct folding of a protein is a key event to attain proper biological function. Correct folding leads to the characteristic conformation of a protein which determines protein activity, aggregation, degradation, and function. Several proteins are implicated in neurodegenerative diseases, such as Parkinson's disease (PD), transmissible spongiform encephalopathies (TSEs), Alzheimer's disease (AD), familial amyloid polyneuropathy (FAP), prion diseases, and Huntington's disease (HD), among several others. These proteins form abnormal aggregates due to alternative folding mechanisms. These misfolded protein aggregates form insoluble fibrils which are then deposited in tissues. Fibrillogenesis is the cause of various pathologies involving neuronal degeneration. Deposition of insoluble fibrils in tissues leads to formation of plaques and tangles and eventual cellular degeneration as the pathology progresses. Despite a lack of amino acid sequence homology of the fibril forming proteins, the fibrils have several common morphological features. For example, some common morphological features of amyloid fibers, (formed by amyloid proteins), include a cross β-structure, similar sizes, display of green birrefringence upon staining with congo red when observed under polarized light, Thioflavin T binding, etc.

One example of a disease based on fibrillogenesis, is the pathology of amyloidosis which is defined by the deposition of amyloid fibrils into tissues and is typified by Alzheimer's Disease (AD). Systemic amyloidosis are characterized by amyloid deposition throughout the viscera. Animal amyloid is a complex material composed partly of protein fibrils. The protein that comprises these fibrils varies from disease to disease. β-Amyloid is one of these proteins which is involved in the pathological progression of AD.

In the case of Parkinson's disease (PD), dopaminergic neurons in the brain undergo selective neurodegeneration. A highly conserved pre-synaptic protein, α-synuclein, with unknown function has been implicated in PD. Two different point mutations in α-synuclein, A53T and A30P, are involved in autosomal dominant familial PD. It is likely that conformational changes in α-synuclein lead to the typical proteinaceous accumulation and fibrillogenesis characteristic of such diseases. Purified full-length α-synuclein can form fibrils similar to those found in Lewy Bodies (cytosolic inclusions) in PD. The mechanism of fibrillogenesis has not been described, although recent data indicate that α-synuclein aggregation follows a nucleation-elongation mechanism, as suggested for the other disease-related proteins.

It is well recognized in the art, that once fibrilloid deposits have formed, there is no known therapy or treatment which significantly dissolves such deposits in situ (U.S. Pat. No. 5,643,562). Consequently, strategies based on prevention of protein aggregation and fibril formation is a major goal in the therapy or prevention of diseases associated with protein misfolding such as neurodegenerative diseases and type 2 diabetes. Thus, there is a need in the art of a system where one can identify therapeutic agents for diseases associated with protein misfolding which may have their therapeutic effect due to being either regulators of protein folding, and/or inhibitors of protein aggregation, and/or preventors and/or inhibitors of the process of fibrillogenesis, or those that can have an entirely different and possibly unknown mechanism of action. Furthermore, there is need that such a system provide a rapid and cost-effective screening method that will allow the identification of agents useful in the treatment, prevention and cure of diseases associated with protein misfolding.

SUMMARY OF THE INVENTION

Diseases involving a misfolded protein have been identified in mammals ("misfolded protein diseases"). These diseases include Parkinson's disease; prion diseases (including Creutzfeldt-Jakob disease (CJD), Fatal Familia insomnia (FFI), Gerstmann-Straussler-Scheinker disease (GSS), mad cow disease, Scrapie, and kuru); Familial Amyloid Polyneuropathy, Tauopathies (including Pick Disease, Lobar Atrophy, and Frontotemporal dementia); Trinucleotide diseases (including Huntington's disease, spinocerebellar ataxia (SCA), dentatorubral pallidoluysian atrophy (DRPLA), Fragile-X syndrome, myotonic dystrophy, Haw River Syndrome, hereditary ataxias, Machado Joseph disease, and Kennedy's disease (spinobulbar muscular atrophy, SBMA)).

The present invention is based on the observation that proteins that misfold and are associated with a disease ("misfolded disease protein") can be expressed in yeast as the basis for screening for therapeutic agents for the treatment of such a disease. Conditions and/or agents have been identified that induce toxicity ("toxicity inducing agent") in a yeast cell expressing a misfolded disease protein, such as huntingtin or alpha synuclein, which are associated with Huntington's disease and Parkinson's disease, respectively. Furthermore, conditions and/or agents that induce toxicity in a yeast cell expressing a particular misfolded disease protein can be identified according to methods of the present invention. Identified conditions and/or agents can be implemented with yeast cells expressing the particular misfolded disease protein to identify therapeutic agents that can be used for the disease associated with the misfolded disease protein. The screen uses viability of the yeast, which express a misfolded disease protein and in which toxicity is induced, to identify compounds that have therapeutic potential in the treatment of the disease associated with the misfolded disease protein. An advantage of the screening methods is that an understanding of the physiology and/or cell biology of the misfolded disease protein or of the etiology of a misfolded protein disease is not necessary to identify candidate therapeutic compounds.

The present invention includes methods of screening for therapeutic agents for Huntington's disease. Such methods involve a yeast cell that expresses all or part of a huntingtin polypeptide, and which has or is contacted with a condition or agent that induces toxicity in the yeast cell such that the yeast cell is no longer viable. Induction of toxicity will lead to loss of viability in the yeast cell. Thus, viability of the yeast cell in the presence of a candidate compound indicates the candidate compound is a candidate therapeutic agent. Viability is used according to its ordinary meaning. It may be evaluated absolutely or relatively, compared to controls. In some embodiments the yeast cell does not express a wild-type Hsp-40 or a functional Hsp-40, which is a condition that induces toxicity in the yeast cell. As used herein, "contacting" a yeast cell with a compound refers to exposing, incubating, touching, associating, making accessible the yeast cell to the compound.

In some embodiments, the huntingtin polypeptide comprises an N-terminal region of a full-length huntingtin polypeptide. It is contemplated that an N-terminal region of a huntingtin polypeptide can comprise the N-terminal region of exon 1 or all of exon 1, including a poly Q repeat region. A poly Q repeat region refers to a region of a huntingtin polypeptide that is characterized by a variable number of glutamine residue repeats starting at position 18 of SEQ ID NO:4 (the HtQ103 protein), SEQ ID NO:6 (the HtQ25 protein), and SEQ ID NO:9 (the Ht Exon1 protein without poly Q repeats). In some embodiments of the invention, the poly Q region comprises 10, 20, 25, 30, 40, 50, 60, 70, 80, 90, 100, 110, 120, 130, 140, 150 or more glutamine residues; in specific embodiments, the poly Q region has 72 or 103 glutamine residues. Exon 1 comprises amino acids 1-68 of the full length Huntingtin protein, however, this exon may comprise a variable number of glutamine residues starting at position 18 where the glutamine (CAG) repeats, in some embodiments, can be 25, 47, 72 or 103 glutamine residues long followed by the remaining 51 amino acids. The human gene sequence for the full length huntingtin polypeptide can be found within GenBank Accession number NT_006081, which is the sequence of chromosome 4, where the huntingtin gene is located, incorporated herein by reference. In the present application, the number of glutamine residues in the poly Q region, which is the region in exon 1 that is characterized by a variable number of glutamine residues, does not alter the amino acid positions of residues downstream of the polyQ region. The term "HtQ25," for example, refers to a huntingtin polypeptide that has a polyQ region with 25 glutamine residues, which is generally considered wild-type.

In some aspects of the screening methods, the yeast cell expresses a polypeptide that comprises a huntingtin polypeptide. The polypeptide may also comprise a non-huntingtin polypeptide. In some embodiments, the polypeptide is a fusion protein comprising a huntingtin polypeptide and another polypeptide, such as a reporter polypeptide. The reporter polypeptide is any polypeptide that allows the polypeptide to be detected or identified in a yeast cell. In some embodiments the reporter polypeptide is a green fluorescent protein (GFP) or Sup35 (including the M and/or C region).

In some embodiments, a yeast cell expresses a mutated Hsp40 polypeptide, which may be exogenous or endogenous. The Hsp40 polypeptide may be truncated at either the C- or N-termini, or it may have an insertion, substitution, or internal deletion. In specific embodiments, the Hsp40 polypeptide has a C-terminal deletion. The C-terminal deletion will include amino acid 352 of SEQ ID NO:8. It and other deletions may comprise 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 3, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 231, 240, 250 or more amino acids contiguous with either amino acid 352 or amino acid 1, or any other amino acid of SEQ ID NO:8. It is further contemplated that the Hsp40 polypeptide may contain multiple mutations. An endogenous polypeptide refers to a polypeptide expressed from a chromosomal (non-recombinant) nucleic acid molecule, whereas an exogenous polypeptide refers to one expressed outside the cell or expressed from a recombinant nucleic acid molecule.

In further embodiments, a yeast cell, expressing or not expressing wild-type Hsp-40, is contacted with a toxicity inducing agent. The yeast may be contacted with a candidate compound before, after, or during contacting with a toxicity inducing agent. A toxicity inducing agent includes a carbon source, nitrogen source, salt, metal, liposome, antibiotic, anisomycin, bleomycin, caffeine, camptothecin, carbonyl-cyanide, daurorubicin, ethanol, formamide, GuHCL, or NEM, or other compounds identified in Table 3. With respect to a yeast cell expressing a huntingtin polypeptide, in some embodiments, a toxicity inducing agent is a carbon source, such as arabinose or potassium acetate, or a salt or metal, such as $CdCl_2$, $CoCl_2$, $CsCl$, $FeCl_2$, $LiC_1$, $NH_4Cl$, $RbCl$, or $ZnCl_2$.

The claimed methods may also include comparing the viability of a yeast cell that was contacted with a candidate compound and that does not express a wild-type Hsp-40 with the viability of a yeast cell contacted with the same candidate compound but that does express a wild-type Hsp40. Alternatively, the viability of a yeast cell that was contacted with a candidate compound and that does not express a wild-type Hsp-40 may be compared with the viability of a yeast cell that does not express a wild-type Hsp-40 but not contacted with the candidate compound. Increased viability by the yeast cell contacted with the candidate compound compared the yeast cell not contacted with the candidate compound indicates that the candidate compound is a candidate therapeutic agent. In other words, as with other embodiments of the invention, absolute or relative viability (increased) in the presence of the candidate compound indicates the candidate compound is a candidate therapeutic compound.

The present invention also concerns screening methods for therapeutic agents for Parkinson's disease involving yeast. In some embodiments of the invention a yeast cell expresses a polypeptide that includes all or part of an alpha synuclein polypeptide, which is the misfolded disease protein associated with Parkinson's disease. The yeast are contacted with a toxicity inducing agent or a composition comprising a toxicity inducing agent. The yeast may be contacted with a candidate compound before, after, or during contacting with a toxicity inducing agent. Absolute or relative viability in the presence of the candidate compound indicates the candidate compound is a candidate therapeutic compound.

In some embodiments of the invention, the alpha synuclein polypeptide is wild-type (SEQ ID NO:2), while in other embodiments it is mutated. The mutation may be a deletion, insertion, or substitution in the polypeptide. In specific aspects of the invention, the alpha synuclein polypeptide comprises a A53T mutation, which is a substitution of threonine for alanine at position 53. In other aspects the alpha synuclein polypeptide comprises a A30P mutation, which is a substitution of proline for alanine at position 53.

In still further embodiments, the alpha synuclein polypeptide is comprised in a fusion protein, which may contain at least another polypeptide. In some embodiments, the polypeptide is a fusion protein comprising a huntingtin polypeptide and another polypeptide, such as a reporter polypeptide. The reporter polypeptide is any polypeptide that allows the polypeptide to be detected or identified in a yeast cell. In some embodiments the reporter polypeptide is a green fluorescent protein (GFP) or Sup35 (including the M and/or C region).

A yeast expressing alpha synuclein in methods of the present invention may have a toxicity inducing condition or be contacted with a toxicity inducing agent. The toxicity inducing agent may be a carbon source, nitrogen source, salt, metal, azauracil, aurintrincarboxylic bleomycin, brefeldin A, camptothecin, chlorambucil, ethidium bromide, formamide, GuHCl, hydroxyurea, menadione, paraquat, or vanadate, or any other compound listed in Table 3. In some embodiments, the carbon source is arabinose, ethanol, or glycerol, while in other embodiments, a nitrogen source is urea. In further embodiments, the toxicity inducing agent is a salt or metal, such as $CaCl_2$, $CoCl_2$, CsCl, or iron, magnesium, RbCl, or $SrCl_2$.

Generally speaking, all of the methods of the present invention may include controls that involve comparing yeast cells in the present and absence of candidate compounds, as well as yeast cells in the presence and absence of toxicity inducing agents or toxicity inducing conditions. Such comparisons are discussed with respect to yeast expressing Hsp-40 above, and may be employed with respect to any screen involving a misfolded disease protein. It is contemplated that any compositions or methods discussed with respect to one embodiment may be employed in the context of other embodiments.

In some embodiments of the invention, viability is lost after 1 hour, 2 hours, 3 hours, 4 hours, 5 hours, 6 hours, 7 hours, 8 hours, 9 hours, 10 hours, 11 hours, 12 hours, 18 hours, 24 hours, 36 hours, 48 hours, 60 hours, 72 hours, 84 hours, 96 hours, or more, but in less time than if the yeast cell had not been exposed to the condition or agent.

The candidate compounds of any of the methods of the invention may be a small molecule or a nucleic acid. The candidate compounds may be comprised in a library or be processed for large-scale throughput screening. The yeast that may be employed include *Saccharomyces cerevisiae* or any other member of Saccharomycetales.

The present invention further encompasses methods of screening for a therapeutic agent for a protein misfolding disease comprising: a) contacting a yeast cell with a candidate compound, wherein the yeast cell expresses a polypeptide comprising a misfolded disease protein; b) contacting the yeast cell with a toxicity inducing agent; c) evaluating the yeast cell for viability, indicating the candidate compound is a candidate therapeutic agent. In some embodiments, the protein misfolding disease is Alzheimer's disease, Parkinson's disease, a Prion disease, Familial Amyloid Polyneuropathy, a Tauopathy, or a Trinucleotide disease. It is specifically contemplated that the protein misfolding disease may a Trinucleotide disease, such as Huntington's disease. In other embodiments the misfolded disease protein is huntingtin, β-amyloid, PrP, alpha synuclein, synphilin, transthyretin, Tau, ataxin 1, ataxin 3, atrophin, or androgen receptor. It is also contemplated that the toxicity inducing agent may a carbon source, nitrogen source, salt, metal, chemotherapeutic agent, alcohol, translation inhibitor, NSAID, DNA intercalator, chelator, liposome, antibiotic, vitamin, proteasome inhibitor, anti-oxidant, or reducing agent. Furthermore, it is contemplated that instead of contacting the yeast cell with a toxicity inducing agent that the yeast may harbor a toxicity inducing condition, such as a mutation in a chaperone protein. As discussed above, embodiments discussed with respect to a screen for therapeutic agents for Huntington's or Parkinson's diseases may be employed with respect to other misfolded protein diseases.

Other methods of the invention include methods of screening for a therapeutic agent for Huntington's disease comprising: a) contacting a yeast cell with a candidate compound, wherein the yeast cell expresses a polypeptide comprising a huntingtin polypeptide; b) incubating the yeast cell under conditions that allow for aggregation of the polypeptide; c) measuring the aggregation of the polypeptide; and comparing the level of aggregation with the level of aggregation in a yeast cell not contacted with the candidate compound. In some embodiments, the yeast cell has a toxicity inducing condition and/or is contacted with a toxicity inducing agent.

The invention also contemplates methods of screening for a therapeutic agent for Parkinson's disease comprising: a) contacting a yeast cell with a candidate compound, wherein the yeast cell expresses a polypeptide comprising an alpha synuclein polypeptide; b) incubating the yeast cell under conditions that allow for aggregation of the polypeptide; c) measuring the aggregation of the polypeptide; and comparing the level of aggregation with the level of aggregation in a yeast cell not contacted with the candidate compound. In some embodiments, the yeast cell has a toxicity inducing condition and/or is contacted with a toxicity inducing agent.

In addition to screening methods, compositions and methods for treatment that arise from the results of screening methods of the invention are also included. Therapeutic agents for treating diseases and conditions involving fibrillogenesis, including Parkinson's disease and Huntington's disease. In some embodiments of the invention, candidate compounds that are screened may be employed in therapeutic methods and compositions of the invention. In further embodiments, the candidate compound is determined to be a candidate therapeutic agent based on its performance in screening assays. If cells incubated with the candidate compound are more viable (based on characteristics that may include cell morphology, number, growth rate, ability to be passaged, and/or ability to be frozen and/or thawed) than cells not incubated with the candidate compound, in some embodiments of the invention the candidate compound is a candidate therapeutic agent. The candidate therapeutic agent may be produced or manufactured, or placed in a pharmaceutically acceptable composition. It is contemplated that any of the screening methods described herein may be employed with respect to therapeutic methods and compositions.

Methods of treating include administering to a patient in need of treatment a therapeutic agent in an amount effective to achieve a therapeutic benefit. A "therapeutic benefit" in the context of the present invention refers to anything that promotes or enhances the well-being of the subject with respect to the medical treatment of his condition, which includes treatment of fibrillogenesis diseases, such as Huntington's and Parkinson's diseases. A list of nonexhaustive examples of this includes extension of the subject's life by any period of time, decrease or delay in the development of the disease, decrease in number of plaques or fibrils, reduction in fibril growth, reduction in number of misfolded proteins, delay in onset of lapse in mental capabilities, and a decrease in atrophy, or dementia to the subject that can be attributed to the subject's condition.

It is contemplated that compositions and steps discussed in the context of an embodiment may be employed with respect to other embodiments discussed herein.

As used herein "aggregation" is used to refer to a clustering or amassing of at least three separate polypeptides. Such "aggregation" precludes specific protein:protein interactions between polypeptides of different sequences, such as observed with yeast two hybrid assays.

As used herein the specification or claim(s) when used in conjunction with the word "comprising", the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
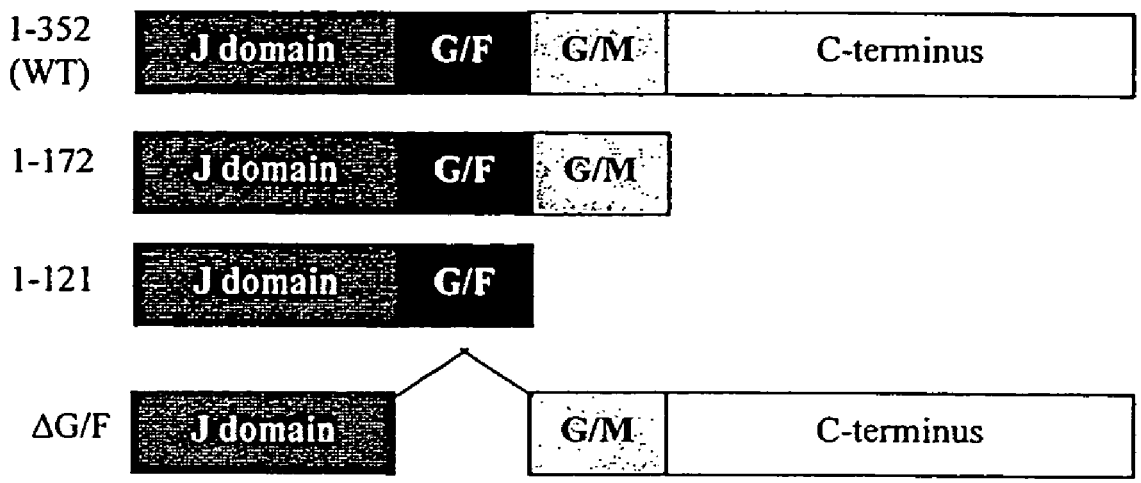
FIG. 1. Sis1p deletions/truncations.
Figure 2:
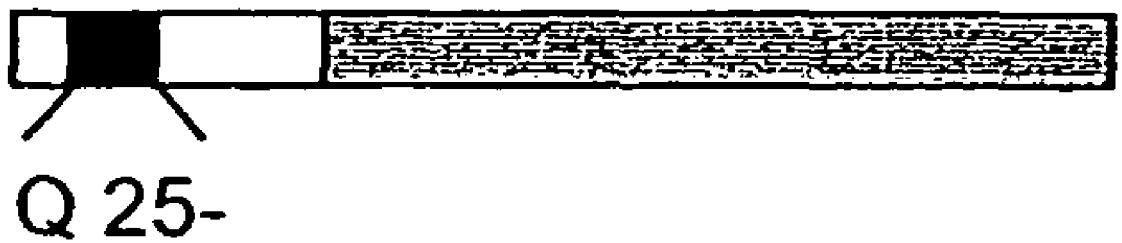
FIG. 2. Expression of Ht fragments in yeast. Schematic representation of Ht-GFP fragments used in this study. Gray box, GFP; white boxes, amino acids 1-68 of the N-terminal region of human Ht protein containing a stretch of 25, 47, 72 or 103 glutamines (black box).
Figure 3:
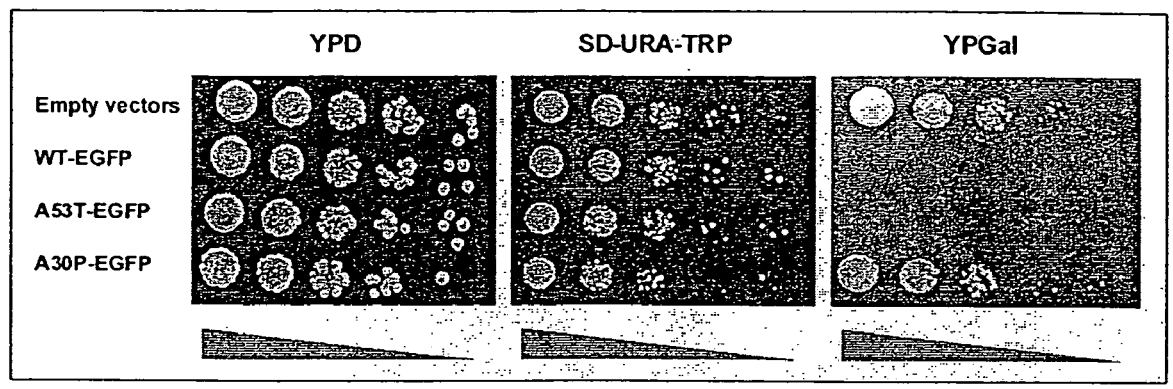
FIG. 3. Expression of alpha-synuclein fused to GFP under the control of the GAL1-10 promoter. Expression of WT and A53T is toxic to the cells. Similar phenotypes were observed with alpha-synuclein alone. These assays have been used in the screening methods to identify agents that can alleviate the observed toxicity.

Deposition of insoluble fibril proteins in tissues is a characteristic of diseases associated with protein misfolding. Most common of these are neurodegenerative diseases and diseases such as type 2 diabetes as well (see Table 1 for a list of diseases associated with protein misfolding). To date there is no known therapy or treatment that can dissolve these protein deposits. Therefore, agents that can prevention protein aggregation and fibril formation are being actively sought. However, methods to identify potential candidate substances are lacking in the art.

The present inventors have developed a system which allows the rapid identification of candidate therapeutic agents that prevent and/or inhibit the process of protein aggregation leading to fibrillogenesis and protein deposition. The system is a yeast-based system, wherein a yeast cell is engineered to expresses a protein or polypeptide that is involved in fibril formation, for example, the yeast cell can express a huntingtin polypeptide in the case of Huntington's disorder, or expresses an alpha synuclein polypeptide in the case of Parkinson's disease, or express an amyloid protein in the case of a disease involving amyloidoses (also see Table 1 for a list of proteins that are associated with fibril formation). In addition to this, in one embodiment, the yeast cell also has a genetic background that causes the yeast cell to have reduced growth rates or no growth as a result of expressing the recombinant polypeptide in combination with the genetic background. In one example, the yeast cell has a mutant Hsp40 gene. A decrease or inhibition of growth indicates toxicity of the recombinant fibril forming polypeptide in the yeast cell as a result of some change in expression or activity of other proteins or cellular factors that interact with the recombinant fibril polypeptide due to the change in genetic background. This cytotoxic profile is correlated to human and/or other mammalian neurodegenerative state. Thus, if such a yeast cell is exposed to a candidate substance, one can screen for the potential of the agent to reverse cytotoxicity, which correlates to the ability of the agent to prevent cytotoxic and/or neurotoxic protein aggregation and fibril formation.

TABLE 1

Disorders with Aberrant Protein Deposition

| Disorder | Protein | Cellular Localization of aggregates |
|---|---|---|
| Parkinson's Disease | α-synuclein | Cytoplasmic |
| Alzheimer's Disease | Amyloid-β | Extracellular |
| Alzheimer's Disease | Tau | Intracellular |
| Prion Diseases | PrP | Extracellular |
| Huntington's Disease | huntingtin | Variable intracellular |
| Spinocerebellar ataxia-1 | Ataxin-1 | Nuclear |
| Spinocerebellar ataxia-2 | Ataxin-2 | NA* |
| Spinocerebellar ataxia-3 | Ataxin-3 | Nuclear, perinuclear |
| Spinocerebellar ataxia-6 | Calcium channel | Cytoplasmic |
| Spinocerebellar ataxia-7 | Ataxin-7 | Nuclear |
| Spinal and bulbar muscular atrophy | Androgen receptor | Nuclear |
| Dentatorubral Pallidoluysian atrophy | Atrophin-1 | Nuclear |
| Amyotropic lateral sclerosis | SOD1 | Cytoplasmic |
| Primary systemic amyloidosis | Immunoglobulin light chain | NA |
| Famylial amyloid polyneuropathy | Transthyretin | Extracellular |
| Senile systemic amyloidosis | Transthyretin | Extracellular |
| Secondary systemic amyloidosis | Serum amyloid A | NA |
| Type 2 diabetes | Islet amyloid polypeptide | NA |
| Injection-localized amyloidosis | Insulin | NA |
| Hemodialysis-related amyloidosis | β2-microglobulin | NA |
| Hereditary cerebral amyloid angiopathy | Cystatin-C | NA |
| Finnish hereditary systemic amyloidosis | Gelsolin | NA |
| Hereditary non-neuropathic | Lysozyme | NA |

*NA, not available

In an alternative embodiment, the yeast cell expressing the recombinant fibril forming protein or polypeptide, is exposed to a set of growth conditions that causes the yeast cell to have reduced or no growth. For example, one may contact the yeast cell with iron or a free radical generator that causes oxidative stress to the cell. Again, a candidate substance can be contacted with this yeast cell to screen for potential agents that can reverse yeast cytotoxicity, which is also correlated to the ability of the agent to prevent cytotoxic protein aggregation and fibril formation.

Although, the mechanism of action of the agents so identified is irrelevant, some possible mechanisms include regulation of protein folding, inhibition of protein aggregation, solubilizing fibrils or aggregates, etc. The yeast-based screening systems of the present invention provide high-throughput and cost-effective screening methods that allow the identification of agents useful in the treatment, prevention and cure of diseases caused due to protein misfolding, and/or aggregation, and/or fibrillogenesis, including several neurodegenerative pathologies.

A. Yeast Cells

Yeast cells offer a powerful system to study the molecular basis of diseases associated with protein misfolding. It is well known that genetic and chemical screens can be easily performed in yeast as the organism offers ease of manipulation. Yeast cells have been used successfully in the study several other disease-related human proteins, for example, CFTR and frataxin, which have corresponding homologues in yeast. Frataxin is a protein involved in a neurodegenerative disease. Therefore, yeast provides an ideal system to study proteins and genes that are involved in human diseases due to the presence of corresponding human homologues. Diseases associated with amyloid and amyloid-like propagation and specificity which constitute a major class of protein misfolding diseases can therefore be studied in yeast cells. Additionally, yeast cells have a non-mendelian inheritance factor, [PSI$^+$], which propagates by a prion-like mechanism, a phenomenon that has been extensively studied.

Any yeast strain may be used in context of the present invention. Some examples of yeast cell strains that can be used in the present method include *Saccharomyces uvae, Saccharomyces kluyveri, Schizosaccharomyces pombe, Saccharomyces uvarum, Kluyveromyces lactis, Hansenula polymorpha, Pichia pastoris, Pichia methanolica, Pichia kluyveri, Yarrowia lipolytica, Candida* sp., *Candida utilis, Candida cacaoi, Geotrichum* sp. and *Geotrichum fermentans*. The preferred yeast strain is *Saccharomyces cerevisiae*.

As the invention concerns screening methods for a wide-variety of pharmaceutical, chemical and genetic agents, one concern is that some of the candidate substances may not be either permeable into yeast cells, or may not be taken up by yeast cells, or may be rapidly metabolized once they enter into the yeast cell, or may be pumped out of the yeast cell. The present inventors contemplate using suitable mutations of yeast strains designed to eliminate these problems. In one example, a yeast strain bearing mutations in 3 genes, the erg6, pdr1, and pdr3, which affect membrane efflux pumps and increasing permeability for drugs are contemplated of use. This particular strain have been used successfully in cancer research to identify growth regulators (see website: http://dtp.nci.nih.gov for details).

B. Heat Shock Proteins

Heat-shock proteins (HSPs), which comprise several evolutionary conserved protein families are induced in a physiological and biochemical response to abrupt increases in temperature or exposure to a variety of other metabolic insults including heavy metals, oxidative stress, toxins, and amino acid analogs. This response occurs in all prokaryotic and eukaryotic cells and is characterized by repression of normal protein synthesis and initiation of transcription of HSP-encoding genes. HSPs are a class of molecular chaperones and under normal conditions, constitutively expressed HSPs facilitate proper protein folding and maturation, promote protein translocation across membranes, and regulate hormone receptor and protein kinase activity. HSPs achieve this by associating with cellular proteins and regulating their conformation.

All of the major HSPs, including those that are constitutively expressed and those that are expressed at very high levels in response to heat and other stresses, have related functions; they ameliorate problems caused by protein misfolding and aggregation. However, each major HSP family has a unique mechanism of action. Some promote the degradation of misfolded proteins (for example, Lon, Ubiquitin, and various Ubiquitin-conjugating enzymes); others bind to various types of folding intermediates and prevent them from aggregating (for example, the HSP70s act by maintaining proteins in an unfolded conformation, while HSP60/GroEL complexes act by facilitating protein folding), yet others have a maturational or regulatory capacity on molecules including steroid hormone receptors (for example, the HSP90s), and yet another HSP promotes the reactivation of proteins that have already aggregated (Hsp100) (Parsell and Lindquist, 1993; Parsell and Lindquist, 1994a and b).

Smaller HSPs can suppress aggregation and heat inactivation of various proteins, including actin. Hsp40, the mammalian homolog of bacterial DnaJ heat shock protein, binds to new polypeptide chains as they are being synthesized on ribosomes and mediates their correct folding. It has been recently shown that, polyglutamine-expanded truncated huntingtin protein interacts with members of Hsp40 and Hsp70 families of chaperones in a polyglutamine length-dependent manner (Krobitsch and Lindquist, 2000; Jana et al., 2000).

Many Hsp40 proteins have been discovered in both prokaryotic and eukaryotic cells, with at least sixteen proteins in yeast and more than 10 proteins in animals cells (see Table 2). These proteins have evolved diverse cellular localizations and functions and have been divided into three subgroups, depending upon the presence of certain conserved amino acids in the J-domain and the presence of various other domains. Sequence alignment of the different yeast Hsp40 homologues to the mammalian Hsp40 protein, HDJ-1, indicate that Sis1 is the most homologous with an amino acid identity of 40%. The yeast Sis1 and the mammalian HDJ-1 are both members of class II. They contain an N-terminal J-domain followed by a glycine-phenylalanine-rich region (GF-region) and a C-terminal region. Both HDJ-1 and Sis1 lack the zinc finger motif between the GF-region and the C-terminal domain. Both are heat-inducible and found in the nucleus and the cytoplasm.

TABLE 2

Heat Shock Proteins

| | Class 1 | Class 2 | Class3 |
| --- | --- | --- | --- |
| Eubacteria | DnaJ | CbpA<br>NolC | DjlA |
| Yeast | Ydj1<br>Mdj1<br>Scj1<br>Xdj1 | Sis1, zuotin<br>Caj1, Hlj1<br>Yir004w, Yjr097w | Sec63, Jem1<br>Yjl162c, Ynl227c<br>Yfr041c |
| Animals | Hdj2<br>Tid56 | Hsj1a&bp<br>Hdj1 | 58ipk<br>Mtj1, auxilin<br>Csp, Mida1 |

In the present invention, the model yeast system, *Saccharomyces cerevisiae*, was used due the availability of multiple isogenic yeast strains with different chaperone activities. However, as will be recognized by the skilled artisan, any other yeast strain may also be used. In one example of the present invention, wild-type yeast strains were engineered to produce the N-terminal region of the huntingtin (Ht), protein with variable poly-glutamate (poly-Q) lengths, including 25, 47, 72 or 103 residues which were fused to the green fluorescent protein (GFP). The production of N-terminal fragments of Ht, is a central event in Huntington's disease (HD), which then leads to formation of Ht aggregates in affected neurons during the natural progression of the disease in both humans and in transgenic animal models. Expression of the Ht proteins was monitored by GFP fluorescence analysis using methods well known in the art. Proteins with 25 glutamines (HtQ25) displayed diffuse fluorescence, whereas proteins with longer glutamine tracts (HtQ47, HtQ72, or HtQ103) exhibited a proportionally greater tendency to aggregate. Differential sedimentation analysis of cell lysates revealed that HtQ25 and HtQ47 were entirely soluble, whereas HtQ72 and HtQ103 were mostly insoluble. These findings demonstrated that in yeast cells, as in mammalian cells, aggregation of Ht fragments depends upon the length of the polyglutamine stretch.

The present inventors then investigated the effect of regulators of protein degradation on poly-glutamine-dependent aggregation. For this, strains with three different partial loss-of-function mutations in the proteasome/ubiquitination pathway (the ubiquitin-activating enzyme; the catalytic subunit of the 20 S proteasome; or a subunit of the 19S proteasome regulatory complex) were utilized and no difference in the fluorescence or sedimentation pattern was observed.

Changing the expression levels of most chaperones also did not affect aggregate formation. However, over-expressing Sis1 (the yeast homologue of mammalian Hdj-1), Hsp70 or Hsp104 modulated the aggregation of HtQ72 and HtQ103. In Hsp104-deficient yeast cells, HtQ72 or HtQ103 remained entirely soluble. Although no toxicity was observed with any of these fragments, with or without aggregation, the inventors demonstrated that the aggregation of huntingtin in yeast cells depends on a balance of chaperone activities in the cell.

As Sis1, which is the yeast homologue of Hsp40, is known to affect the aggregation state of huntingtin and is crucial for polyQ-induced toxicity in various model systems, the present inventors performed a detailed analysis of Sis1. Yeast strains engineered to express different regions of the Sis1 protein were transformed with the huntingtin-GFP fusion constructs. Aggregation pattern of HtQ72 and HtQ103 were markedly altered by the production of mutant Sis1 proteins. Instead of a small number of large aggregates a large number of smaller aggregates were present. Most notably, in one Sis1 construct the change in aggregation was accompanied by a reduction in yeast cell viability. The inventors found that this Sis1-induced toxicity is reduced by co-expression of Hsp104. Hsp104 also reduces both aggregate formation and cell death in a mammalian cell model of huntingtin toxicity and in a *C. elegans* model employing simple polyQ-GFP-fusions. Thus, the toxicity of huntingtin induced by Sis1 alterations in yeast correlate to Ht toxicity in humans.

Thus, the present inventors have developed systems that utilize yeast as a model system for the analysis of proteins that are involved in the formation of fibrils and/or proteins that aggregate to form insoluble deposits, exemplified by proteins such as huntingtin. The skilled artisan will recognize that huntingtin is merely a non-limiting example. The system and methods developed herein allow the identification of agents that affect the conformational state of such proteins in a living cell without the potential complications of toxicity (such as, the induction of stress responses, the appearance of suppressor mutations, etc.).

To identify potential pharmaceutical and therapeutic agents that affect proteins that are involved in the formation of fibrils and/or proteins that aggregate to form insoluble deposits, the inventors contemplate experiments that employ a yeast strain that expresses a truncated Sis1 protein and a aggregating protein or fibril forming protein that causes toxicity, such as HtQ103. In the example of Ht proteins, the inventors contemplate using yeast strains with the mutant Sis1 background expressing HtQ25 (control, not toxic), HtQ47 or HtQ72 (not toxic, but potentially so), or HtQ103 (toxic). These yeast cells will be spotted in serial dilutions onto selective media with or without test agents. Increased growth rate on test plates compared to control plates will identify compounds with a potential for reducing toxicity; a decreased growth will identify compounds that might increase toxicity. Microscopic analysis will determine whether these agents also affect aggregate formation and will use GFP-fusion proteins. This screen will also be performed with yeast strains expressing only the N-terminal region of Ht, not fused to GFP. In addition, the inventors contemplate screening a library of FDA approved compounds for human use for identifying therapeutic agents for diseases involving aberrant protein deposition, and/or fibrillogenesis, and/or amyloidosis, and/or proteins aggregation to form insoluble deposits. The inventors also contemplate screening a large scale combinatorial chemistry libraries and genomic and cDNA libraries to identify chemical and genetic agents that can provide therapeutic benefit. Similar experiments are contemplated with other fibril forming/aggregate forming proteins such as those listed in Table 1.

Therefore, mutations in HSPs can result in diseases caused as a result of protein misfolding, and protein aggregation among others. In the present invention, yeast cells with mutations in HSP genes have been used to express recombinant proteins that are involved in diseases associated with protein misfolding. This results in yeast cells which have lower or no growth rates, indicating cytotoxic effects due to misfolding of the recombinant protein in the cell that lacks the ability to correct the misfolding. These yeast cells have been used to develop screening methods to identify agents that can correct protein folding and thereby provide therapeutic or preventive benefits for diseases involving protein misfolding.

C. Other Toxicity Inducing Agents

In other embodiments of the invention, some of the fibril forming/aggregate forming proteins have been shown to have toxic effects when the yeast cell is subject to other toxicity inducing agents. The toxicity inducing agents can be a carbon source, nitrogen source, salt, metal, chemotherapeutic agent, alcohol, translation inhibitor, NSAID, DNA intercalator, chelator, liposome, antibiotic, vitamin, proteasome inhibitor, anti-oxidant, or reducing agent (see some non-limiting examples listed in Table 3). Thus, changes in growth conditions for example, by exposure to one of the agents listed above, causes toxicity in yeast cells. The toxicity maybe due to oxidative stress or conditions that alter other stress response pathways of the yeast cell. Oxidative stress is defined here as any process that affect the oxidative/respiratory mechanism of a cell. This may be a result of generation of free radicals or respiratory enzyme poisons.

TABLE 3

Putative Toxicity Inducing Agents

Carbon Sources

YPD
Dextrose 2% (SD) pH 4.9
Dextrose 2% (SD) pH 6.0
Dextrose 2% (SD) pH 6.8
Fermentable Galactose 2%
Maltose
Melibiose
Raffinose
Sucrose
Oleic acid
Lauric acid
Arabinose 2%
Non-Fermentable K-Acetate 3%
Ethanol 3%
Glycerol 2%
Glycerol 20%
Nitrogen Sources allantoin 1 mg ml−1
ammonia (NH4Cl) 1 mg ml−1
glutamate 1 mg ml−1
glutamine 1 mg ml−1
ornithine 1 mg ml−1
proline 1 mg ml−1
serine 1 mg ml−1
threonine 1 mg ml−1
Salts and Metals AlF3 1 mM
BaCl2 50 mM
CaCl2 0.5 M
CdCl2 20 μM
CdCl2 50 μM
CoCl2 750 μM
CoCl2 300 μM
CsCl 0.1 M
CsCl 25 mM
CuSO$_4$ 0.5 mM
CuSO$_4$ 2.5 mM
CuSO$_4$ 5 mM
Fe$_2$(SO$_4$)$_3$ 8.5 mM
Fe$_2$(SO$_4$)$_4$ 20 mM
FeCl$_2$ 10 mM
FeCl$_2$ 23 mM
FeCl$_2$ 50 mM
FeCl$_3$ 20 mM
FeCl$_3$ 8.5 mM
FeSO$_4$ 50 mM
FeSO$_4$ 23 mM
KI
LiCl 0.3 M
MgCl$_2$ 0.5 M
MgSO$_4$ 0.5 M
MnCl$_2$ 4 mM
NaCl 0.3 M
NaCl 0.7 M
NH$_4$Cl 0.9 M
NiCl$_2$ 850 μM
RbCl 0.2 M
ZnCl$_2$ 2.5 mM
ZnCl$_2$ 10 mM
ZnCl$_2$ 5 mM
Inhibitors 1,10-phenanthroline 30 μg/ml
2,2-dipyridil 50 μg/ml
4-NQO 2.5 μg/ml
4-NQO 2.5 μg.ml
5-azacytidine 100 μg/ml (toxic)
5-fluorocytosine 0.02 mg/ml
5-fluorouracil
6-azauracil 30 μg/ml

TABLE 3-continued

Putative Toxicity Inducing Agents 8-hydroxyquinoline 26 μg/ml
actinomycin D 45 μg/ml (no DMSO)
actinomycin D DMSO
anisomycin 20 μg/ml
anisomycin 50 μg/ml
antimycin A 1 μg/ml
aspirin (Acetylsalicylic acid)
aurintricarboxylic acid 100 μM
BAPTA 20 mM
benomyl 1 μg/ml (37° C.)
benomyl 10 μg/ml (37° C.)
benomyl 20 μg/ml (37° C.)
benomyl 40 μg/ml
bleomycin 10 μg/ml
brefeldin A 100 μg/ml
caffeine 1 mM
caffeine 10 mM
calcofluor white (fluorescence B28) 1 mg/ml
camptothecin 0.1 μg/ml
camptothecin 5 μg/ml
canavanine 30 μM (SD-arg)
carbonyl-cyanide m-chlorophenylhydrazone 1–3 μM
cercosporamide 5 μg/ml
cerulenin 0.5 μg/ml
chlorambucil 3 mM)
ciclopyroxolamine
cinnarizine 100 μg/ml
cycloheximide 0.2 μg ml−1 (toxic & dangerous for environment)
cycloheximide 3 μg ml−1
daunomycin 0.05 mg/ml
D-his 0.5 mM (L-pro)
diamide 1 mM
diamide 2 mM
diltiazem hydrochloride 2 mg/ml
distamycin A SD 80–400 μM
DL-C-allylglycine 0.025 mg/ml
EDTA 1 mg/ml
EGTA 10 mM
emetine 2 ug/ml mg/ml
erythromycin 200 μg/ml
ethanol 10%
ethanol 6%
Ethidium bromide 25 μg/ml
Ethidium bromide 50 μg/ml
Etoposide
Fenpropinorph 0.3 μM
Flufenamic acid
Formamide 2%
Formamide 3%
griseofulvin 100 μg/ml
GuHCl 20 mM
GuHCl 5 mM
Hydroxyurea 10 mg/ml
Hydroxyurea 5 mg/ml
Ibruprofen
L-ethionine 1 ug/ml
menadione 20 to 50 uM
mevinolin 400 ug/ml
micocystin-LR 0.2 and 1 uM
Na orthovanadate 3 mM
nalidixic acid use 200 ug/ml
NBQX
NEM 0.01 mM
neomycin 5 mg/ml
Nicotinic acid
nocodazole 1 μg/ml
nocodazole 50 μg/ml
nocodazole 10 μg/ml
nystatin 2 μg/ml
o-DNB 175 μM
oligomycin 1 μg/ml (YPGE)
oligomycin 2.5 μg/ml (YPGE)
olygomicin 5 μg/ml (YPGE)
papulacandin B 20 μg/ml
paracetamol
paraquat 1 mM (methyl viologen)

TABLE 3-continued

Putative Toxicity Inducing Agents paraquat 10 mM
paraquat 5 mM
paromomycin 100 µg/ml
paromomycin 200 µg/ml
paromomycin sulphate 2 mg/ml
phenylethanol 2 mg/ml
phenylethanol 5 mg/ml
PMSF 4–5 mM
protamine sulphate 750 µM
protamine sulphate 250 µM
quinolinic acid
rapamycin 0.1 µg/ml
SD-arg 1 ug/ml canavanine
SD-arg 30 ug/ml canavanine
sodium fluoride 5 mM
staurosporine 0.1 µg/ml (37° C.)
staurosporine 1 µg/ml (37° C.)
streptonigrin 1 µg/ml
Thiamine
Thiolutin 3 to 9 µg/ml
trifluoperazine 20 uM
tunicamycin 2.5 µg/ml
vanadate 1 mM
vanadate 0.1 mM
vanadate 2 mM
vanadate 4 mM
vanadate 7 mM + KCl
vanadate no KCl
verapamil hydrochloride 100 µg/ml
verrucarin A 2.45 µg/ml
Liposomes DOSPA (lipofectamine)
DOSPER
DOGS (transfectam)
DDAB
DOPE
Antibiotics Ampicillin
Amphotericin B (Fungizone) 0.045 µg/ml
Amphotericin B 45 µg/ml
Chloramphenicol
Cyclosporin A
Kanamycin
Vitamins Vitamin A
Vitamin B12
Vitamin C (ascorbate)
Vitamin D
Vitamin E (tocopherol)
Vitamin K
Proteasome Inhibitors ALLN 50 µM
E64d 100 µM
LLM 50 µM
MG132 50 µM
quinacrine 2 µM
chloroquine 4.2 µM
chloroquine 10 µM
clioquinol 5 µM
(R)-(—)-3-hydroxybutirate***
D-beta-hydroxybutyrate
DOPAMINE
L-dihydroxyphenylalanine (L-DOPA)
Amyloid related Congo Red 5 µM
Thiflavine S
Thioflavine T
chrysamine G 1.0 µM (3 to 30 µM in cos cells)
direct orange 6 µM
direct yellow 20 0.5 µM
N,N'-terephtalylidenebis-
(4aminosalicylic acid) >100 µM
4,4'-bis-(carboxyphenylamino)-3,3'-
dimethoxybiphenyl >100 µM
myo-inositol 1.5 mg/ml
epi-inositol 1.5 mg/ml
scyllo-inostol 1.5 mg/ml
Deoxycorticosterone
Anti-oxidants 6-hydroxydopamine
carvedilol
deferoxamine mesylate
Ferritin
Estradiol
Glutathione
NO
Reducing agents 2-mercaptoethanol
DTT
Miscellaneous K-Acetate + PB
UV
Osmotic Stress KCl 1.3 M
Sorbitol 1.5 M
Temperature ° C.

30
38
RT
14
Thermotolerance
Ethanol Gradient
Osmolytes

Trehalose
Glycerol 20%
Control Plates for solvents/additives 0.5 M KCl
acetone 1%
chloroform
DMF
DMSO 5%
DMSO 1%
DMSO/EtOH
methanol 5%

D. Nucleic Acids

One embodiment of the present invention is to transfer nucleic acids encoding a protein or polypeptide involved in protein aggregation and/or fibril formation, such as a misfolded disease protein, into a yeast cell so that the yeast cell expresses the protein. For example, one may express alpha synuclein, huntingtin, transthyretin, β2-microglobulin, or any amyloid protein, such as beta-amyloid, alpha amyloid, islet amyloid polypeptide, and the like (see Table 1 for other non-limiting examples). In one embodiment the nucleic acids encode a full-length, substantially full-length, or functional equivalent form of such a protein or polypeptide. In additional embodiments, a truncated polypeptide or a polypeptide with internal deletions is provided to a yeast cell. In other embodiments the polypeptide is a human or other mammalian homologue.

In other embodiments, the yeast cell may be also transfected with heat-shock protein. In yet other aspects the invention contemplates co-transfecting the yeast cell with any protein that is involved in interacting with other cellular proteins and assisting with protein folding, protein aggregation etc.

Thus, in some embodiments of the present invention, the development of the yeast-based screening system involves the transfection of a yeast cell with an expression construct encoding a protein or polypeptide involved in protein aggregation and/or fibril formation.

Certain aspects of the present invention concern at least one nucleic acid encoding a protein or polypeptide involved in protein aggregation and/or fibril formation molecule or a heat shock protein or a protein involved in interacting with other proteins. In certain aspects, the nucleic acid comprises a wild-type or mutant nucleic acid. In particular aspects, the nucleic acid encodes for at least one transcribed nucleic acid. In particular aspects, the nucleic acid encoding the protein or polypeptide involved in protein aggregation and/or fibril formation, or a heat shock protein or a protein involved in interacting with other proteins, encodes at least one protein, polypeptide, or peptide, or biologically functional equivalent thereof. In other aspects, the nucleic acid encoding a protein or polypeptide involved in protein aggregation and/or fibril formation encodes at least one nucleic acid segment of SEQ ID NO:1 (alpha synuclein), SEQ ID NO:3 (HtQ103), SEQ ID NO:5 (HtQ25), SEQ ID NO:9 (Ht Exon 1 without any polyglutamine repeats) or at least one biologically functional equivalent thereof. In another aspect, the nucleic acid encoding a heat-shock protein encodes at least one nucleic acid segment of SEQ ID NO:7 (HSP40 homologue of yeast, also called Sis 1 in yeast cells) or at least one biologically functional equivalent thereof.

The present invention also concerns the isolation or creation of at least one recombinant construct or at least one recombinant host cell through the application of recombinant nucleic acid technology known to those of skill in the art or as described herein. The recombinant construct or host cell may comprise at least one nucleic acid encoding a protein or polypeptide involved in protein aggregation and/or fibril formation, and may express at least one protein, polypeptide, or peptide, involved in protein aggregation and/or fibril formation or at least one biologically functional equivalent thereof.

In some embodiments the invention refers to DNA sequences identified by Database Accession numbers: Genbank NC_001146, which is the accession number for the chromosome on which the SIS1 gene is located, and SIS1 is referenced by SGD ID S0004952; Genbank NM_000345 for alpha-synuclein; and Genbank NT_006081, for the accession number for chromosome 4 where the Huntingtin gene is located.

As used herein "wild-type" refers to the naturally occurring sequence of a nucleic acid at a genetic locus in the genome of an organism, and sequences transcribed or translated from such a nucleic acid. Thus, the term "wild-type" also may refer to the amino acid sequence encoded by the nucleic acid. As a genetic locus may have more than one sequence or alleles in a population of individuals, the term "wild-type" encompasses all such naturally occurring alleles. As used herein the term "polymorphic" means that variation exists (i.e., two or more alleles exist) at a genetic locus in the individuals of a population. As used herein, "mutant" refers to a change in the sequence of a nucleic acid or its encoded protein, polypeptide, or peptide that is the result of recombinant DNA technology.

A nucleic acid may be made by any technique known to one of ordinary skill in the art. Non-limiting examples of synthetic nucleic acid, particularly a synthetic oligonucleotide, include a nucleic acid made by in vitro chemical synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986, and U.S. Pat. No. 5,705,629, each incorporated herein by reference. A non-limiting example of enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of oligonucleotides described in U.S. Pat. No. 5,645,897, incorporated herein by reference. A non-limiting example of a biologically produced nucleic acid includes recombinant nucleic acid production in living cells, such as recombinant DNA vector production in bacteria (see for example, Sambrook et al. 1989, incorporated herein by reference).

A nucleic acid may be purified on polyacrylamide gels, cesium chloride centrifugation gradients, or by any other means known to one of ordinary skill in the art (see for example, Sambrook et al. 1989, incorporated herein by reference).

The term "nucleic acid" will generally refer to at least one molecule or strand of DNA, RNA or a derivative or mimic thereof, comprising at least one nucleobase, such as, for example, a naturally occurring purine or pyrimidine base found in DNA (e.g., adenine "A," guanine "G," thymine "T," and cytosine "C") or RNA (e.g. A, G, uracil "U," and C). The term "nucleic acid" encompasses the terms "oligonucleotide" and "polynucleotide." The term "oligonucleotide" refers to at least one molecule of between about 3 and about 1100 nucleobases in length. The term "polynucleotide" refers to at least one molecule of greater than about 100 nucleobases in length. These definitions generally refer to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule.

In certain embodiments, a "gene" refers to a nucleic acid that is transcribed. As used herein, a "gene segment" is a nucleic acid segment of a gene. In certain aspects, the gene includes regulatory sequences involved in transcription, or message production or composition. In particular embodiments, the gene comprises transcribed sequences that encode for a protein, polypeptide or peptide. In keeping with the terminology described herein, an "isolated gene" may comprise transcribed nucleic acid(s), regulatory sequences, coding sequences, or the like, isolated substantially away from other such sequences, such as other naturally occurring genes, regulatory sequences, polypeptide or peptide encoding sequences, etc. In this respect, the term "gene" is used for simplicity to refer to a nucleic acid comprising a nucleotide sequence that is transcribed, and the complement thereof. In particular aspects, the transcribed nucleotide sequence comprises at least one functional protein, polypeptide and/or peptide encoding unit. As will be understood by those in the art, this functional term "gene" includes both genomic sequences, RNA or cDNA sequences, or smaller engineered nucleic acid segments, including nucleic acid segments of a non-transcribed part of a gene, including but not limited to the non-transcribed promoter or enhancer regions of a gene. Smaller engineered gene nucleic acid segments may express, or may be adapted to express using nucleic acid manipulation technology, proteins, polypeptides, domains, peptides, fusion proteins, mutants and/or such like. Thus, a "truncated gene" refers to a nucleic acid sequence that is missing a stretch of contiguous nucleic acid residues that encode a portion of a full-length protein or polypeptide involved in protein aggregation and/or fibril formation. For example, a truncated gene may not contain the nucleic acid sequence for the N-terminal region of the protein or polypeptide involved in protein aggregation and/or fibril formation or of a heat-shock protein gene.

"Isolated substantially away from other coding sequences" means that the gene of interest, in this case the gene encoding either a protein or polypeptide involved in protein aggregation and/or fibril formation; or a heat-shock protein; or any molecular chaperone protein, forms the significant part of the coding region of the nucleic acid, or that the nucleic acid does not contain large portions of naturally-occurring coding nucleic acids, such as large chromosomal fragments, other functional genes, RNA or cDNA coding regions. Of course, this refers to the nucleic acid as originally isolated, and does not exclude genes or coding regions later added to the nucleic acid by recombinant nucleic acid technology.

In certain embodiments, the nucleic acid is a nucleic acid segment. As used herein, the term "nucleic acid segment," are smaller fragments of a nucleic acid, such as for non-limiting example, those that encode only part of a peptide or polypeptide sequence involved in protein aggregation and/or fibril formation. Thus, a "nucleic acid segment may comprise any part of the gene sequence, of from about 2 nucleotides to the full-length of the encoding region. In certain embodiments, the "nucleic acid segment" encompasses the full-length gene sequence.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be created:

n to n+y where n is an integer from 1 to the last number of the sequence and y is the length of the nucleic acid segment minus one, where n+y does not exceed the last number of the sequence. Thus, for a 10-mer, the nucleic acid segments correspond to bases 1 to 10, 2 to 11, 3 to 12 . . . and/or so on. For a 15-mer, the nucleic acid segments correspond to bases 1 to 15, 2 to 16, 3 to 17 . . . and/or so on. For a 20-mer, the nucleic segments correspond to bases 1 to 20, 2 to 21, 3 to 22 . . . and/or so on. In certain embodiments, the nucleic acid segment may be a probe or primer.

The nucleic acid(s) of the present invention, which encode either a protein or polypeptide involved in protein aggregation and/or fibril formation; or a heat-shock protein; or any molecular chaperone protein, regardless of the length of the sequence itself, may be combined with other nucleic acid sequences, including but not limited to, promoters, enhancers, polyadenylation signals, restriction enzyme sites, multiple cloning sites, coding segments, and the like, to create one or more nucleic acid construct(s). The overall length may vary considerably between nucleic acid constructs. Thus, a nucleic acid segment of almost any length may be employed, with the total length preferably being limited by the ease of preparation or use in the intended recombinant nucleic acid protocol.

(a) Nucleic Acid Vectors for the Expression of Screening Method Components in Yeast Cells A gene encoding a component of the assay system of the invention, such as misfolded disease protein; or a heat shock protein; or any other molecular chaperone; or even a candidate substance that has therapeutic value for protein misfolding diseases may be transfected into a yeast cell using a nucleic acid vector, including but are not limited to, plasmids, linear nucleic acid molecules, artificial chromosomes and episomal vectors. Yeast plasmids are naturally preferred and three systems used for recombinant plasmid expression and replication in yeast include:

1. Integrating plasmids: An example of such a plasmid is YIp, which is maintained at one copy per haploid genome, and is inherited in Mendelian fashion. Such a plasmid, containing a gene of interest, a bacterial origin of replication and a selectable gene (typically an antibiotic-resistance marker), is produced in bacteria. The purified vector is linearized within the selectable gene and used to transform competent yeast cells. Regardless of the type of plasmid used, yeast cells are typically transformed by chemical methods (e.g. as described by Rose et al., 1990, Methods in Yeast Genetics, Cold Spring Harbor Laboratory Press, Cold Spring Harbor, N.Y.). The cells are typically treated with lithium acetate to achieve transformation efficiencies of approximately $10^4$ colony-forming units (transformed cells)/µg of DNA. Yeast perform homologous recombination such that the cut, selectable marker recombines with the mutated (usually a point mutation or a small deletion) host gene to restore function. Transformed cells are then isolated on selective media.

2. Low copy-number ARS-CEN: One example is YCp and such plasmids contain the autonomous replicating sequence (ARS 1), a sequence of approximately 700 bp which, when carried on a plasmid, permits its replication in yeast, and a centromeric sequence (CEN4), the latter of which allows mitotic stability. These are usually present at 1-2 copies per cell. Removal of the CEN sequence yields a YRp plasmid, which is typically present in 100-200 copes per cell; however, this plasmid is both mitotically and meiotically unstable.

3. High-copy-number 2p circles: These plasmids contain a sequence approximately 1 kb in length, the 2µ sequence, which acts as a yeast replicon giving rise to higher plasmid copy number; however, these plasmids are unstable and require selection for maintenance. Copy number is increased by having on the plasmid a selection gene operatively linked to a crippled promoter. This is usually the LEU2 gene with a truncated promoter (LEU2-d), such that low levels of the Leu2p protein are produced; therefore, selection on a leucine-depleted medium forces an increase in copy number in order to make an amount of Leu2p sufficient for cell growth.

Examples of yeast plasmids useful in the invention include the YRp plasmids (based on autonomously-replicating sequences, or ARS) and the YEp plasmids (based on the 2µ circle), of which examples are YEp24 and the YEplac series of plasmids (Gietz and Sugino, 1988). (See Sikorski, "Extrachromsomoal cloning vectors of *Saccharomyces cerevisiae*", in Plasmid, A Practical Approach, Ed. K. G. Hardy, IRL Press, 1993; and Yeast Cloning Vectors and Genes, Current Protocols in Molecular Biology, Section II, Unit 13.4, Eds., Ausubel et al., 1994).

In addition to a yeast origin of replication, yeast plasmid sequences typically comprise an antibiotic resistance gene, a bacterial origin of replication (for propagation in bacterial cells) and a yeast nutritional gene for maintenance in yeast cells. The nutritional gene (or "auxotrophic marker") is most often one of the following: TRP1 Phosphoribosylanthranilate isomerase, which is a component of the tryptophan biosynthetic pathway); URA43 (Orotidine-5'-phosphate decarboxylase, which takes part in the uracil biosynthetic pathway); LEU2 (3-Isopropylmalate dehydrogenase, which is involved with the leucine biosynthetic pathway); HIS3 (Imidazoleglycerolphosphate dehydratase, or IGP dehydratase); or LYS2 (α-aminoadipate-semialdehyde dehydrogenase, part of the lysine biosynthetic pathway.

(b) Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well. Control sequences comprising promoters, enhancers and other locus or transcription controlling/modulating elements are also referred to as "transcriptional cassettes".

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al., 1989, incorporated herein by reference). The promoters employed may be constitutive, tissue-specific, inducible, and/or useful under the appropriate conditions to direct high level expression of the introduced DNA segment, such as is advantageous for gene therapy or for applications such as the large-scale production of recombinant proteins and/or peptides. The promoter may be heterologous or endogenous.

Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Various inducible elements/promoters/enhancers that may be employed, in the context of the present invention, to regulate the expression of a RNA. Inducible elements are regions of a nucleic acid sequence that can be activated in response to a specific stimulus. Some examples of yeast specific promoters include inducible promoters such as Gal1-10, Gal1, GalL, GalS, repressible promoter Met25, and constitutive promoters such as glyceraldehyde 3-phosphate dehydrogenase promoter (GPD), alcohol dehydrogenase promoter (ADH), translation-elongation factor-1-alpha promoter (TEF), cytochrome c-oxidase promoter (CYC1), MRP7 etc. Autonomously replicating expression vectors of yeast containing promoters inducible by glucocorticoid hormones have also been described (Picard et al., 1990), these include the glucorticoid responsive element (GRE). These and other examples are described in Mumber et al., 1995; Ronicke et al., 1997; Gao, 2000, all incorporated herein by reference. Yet other yeast vectors containing constitutive or inducible promoters such as alpha factor, alcohol oxidase, and PGH may be used. For reviews, see Ausubel et al., and Grant et al., 1987. Additionally any promoter/enhancer combination (as per the Eukaryotic Promoter Data Base EPDB) could also be used to drive expression of genes.

The identity of tissue-specific promoters or elements, as well as assays to characterize their activity, is well known to those of skill in the art. Non-limiting examples of such regions include the human LIMK2 gene (Nomoto et al., 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), and human platelet endothelial cell adhesion molecule-1 (Almendro et al., 1996).

Typically promoters and enhancers that control the transcription of protein encoding genes in eukaryotic cells are composed of multiple genetic elements. The cellular machinery is able to gather and integrate the regulatory information conveyed by each element, allowing different genes to evolve distinct, often complex patterns of transcriptional regulation.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Aside from this operational distinction, enhancers and promoters are very similar entities.

Promoters and enhancers have the same general function of activating transcription in the cell. They are often overlapping and contiguous, often seeming to have a very similar modular organization. Taken together, these considerations suggest that enhancers and promoters are homologous entities and that the transcriptional activator proteins bound to these sequences may interact with the cellular transcriptional machinery in fundamentally the same way.

A signal that may prove useful is a polyadenylation signal (hGH, BGH, SV40). The use of internal ribosome binding sites (IRES) elements are used to create multigene, or polycistronic, messages. IRES elements are able to bypass the ribosome scanning model of 5'-methylated cap-dependent translation and begin translation at internal sites (Pelletier and Sonenberg, 1988). IRES elements from two members of the picornavirus family (polio and encephalomyocarditis) have been described (Pelletier and Sonenberg, 1988), as well as an RES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

(c) Multiple Cloning Sites

Vectors used to transform the yeast cells in the present invention can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

(d) Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

(e) Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

(f) Polyadenylation Signals

In eukaryotic gene expression, one will typically include a polyadenylation signal to effect proper polyadenylation of the transcript. The nature of the polyadenylation signal is not believed to be crucial to the successful practice of the invention, and any such sequence may be employed. Some examples include the SV40 polyadenylation signal or the bovine growth hormone polyadenylation signal, convenient and known to function well in various target cells. Polyadenylation may increase the stability of the transcript or may facilitate cytoplasmic transport.

(g) Origins of Replication

In order to propagate a vector of the invention in a host cell, it may contain one or more origins of replication sites (often termed "ori"), which is a specific nucleic acid sequence at which replication is initiated. Alternatively, an autonomously replicating sequence (ARS) can be employed if the host cell is yeast.

(h) Selectable and Screenable Markers

In certain embodiments of the invention, yeast cells transduced with the constructs of the present invention may be identified in vitro or in vivo by including a marker in the expression vector. Such markers would confer an identifiable change to the transduced cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genetic constructs that confer resistance to kanamycin, neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is fluorescence analysis, are also contemplated. Other reporter polypeptides used in the present invention include Sup35p or other yeast prions. Additionally, auxotrophic markers such as leu, ura, trp, his, and the like for selection on different media. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

(i) Oligonucleotide Probes and Primers

Naturally, the present invention also encompasses DNA segments that are complementary, or essentially complementary, to the sequences encoding proteins or polypeptides involved in protein aggregation and/or fibril formation or heat-shock proteins, for example those set forth in SEQ ID NO:1, SEQ ID NO:3, SEQ ID NO:5 and SEQ ID NO:7. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment encoding proteins or polypeptides involved in protein aggregation and/or fibril formation or to heat-shock proteins, under relatively stringent conditions such as those described herein. Such sequences may encode the entire protein involved in protein aggregation and/or fibril formation, or heat-shock proteins, or may be a fragment thereof.

The nucleic acid detection techniques and conditions described herein serve both to define the functionally equivalent nucleic acids of the invention, as outlined structurally above, and to describe certain methods by which the yeast cells transformed with proteins or polypeptides involved in protein aggregation and/or fibril formation sequences, or heat-shock protein sequences, may be screened, selected, and characterized.

Hybridizing fragments should be of sufficient length to provide specific hybridization to a RNA or DNA tissue sample. The use of a hybridization probe of between about 10-14 or 15-20 and about 100 nucleotides in length allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained.

Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 300, 500, 600, 700, 800, 900, 1000, 1100, 1200 and longer are contemplated as well. Such oligonucleotides will find use, for example, as probes in Southern and Northern blots and as primers in amplification reactions.

Accordingly, the nucleotide sequences of the invention may be used for their ability to selectively form duplex molecules with complementary stretches of genes or RNAs or to provide primers for amplification of DNA or RNA from tissues. Depending on the application envisioned, one will desire to employ varying conditions of hybridization to achieve varying degrees of selectivity of probe towards target sequence.

For applications requiring high selectivity, one will typically desire to employ relatively stringent conditions to form the hybrids, e.g., one will select relatively low salt and/or high temperature conditions, such as provided by about 0.02 M to about 0.10 M NaCl at temperatures of about 50° C. to about 70° C. Such high stringency conditions tolerate little, if any, mismatch between the probe and the template or target strand, and would be particularly suitable for isolating specific genes or detecting specific mRNA transcripts. It is generally appreciated that conditions can be rendered more stringent by the addition of increasing amounts of formamide.

For certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 µM MgCl$_2$, at temperatures ranging from approximately 40° C. to about 72° C.

One method of using probes and primers of the present invention is in the search for genes related to misfolded disease proteins or, more particularly, homologs of misfolded disease proteins from other species. Normally, the target DNA will be a genomic or cDNA library, although screening may involve analysis of RNA molecules. By varying the stringency of hybridization, and the region of the probe, different degrees of homology may be discovered.

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected.

In certain embodiments, one may desire to employ a fluorescent label, electroluminescence or an enzyme tag such as urease, alkaline phosphatase or peroxidase, instead of radioactive or other environmentally undesirable reagents. In the case of enzyme tags, colorimetric indicator substrates are known which can be employed to provide a detection means visible to the human eye or spectrophotometrically, to identify specific hybridization with complementary nucleic acid-containing samples.

In general, it is envisioned that the hybridization probes described herein will be useful both as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions.

The selected conditions will depend on the particular circumstances based on the particular criteria required (depending, for example, on the G+C content, type of target nucleic acid, source of nucleic acid, size of hybridization probe, etc.). Following washing of the hybridized surface to remove non-specifically bound probe molecules, hybridization is detected, or even quantified, by means of the label.

E. Protein, Polypeptides, and Peptides

The invention contemplates the use of a polypeptide or a proteins encoding a misfolded disease protein or a heat shock protein. In some embodiments a full-length or a substantially full-length misfolded disease protein/polypeptide or heat shock protein may be used. The term "full-length" refers to a misfolded disease polypeptide or heat shock protein that contains at least all the amino acids encoded by the misfolded disease protein cDNA or heat shock protein cDNA. The term "substantially full-length" in the context of a misfolded disease protein refers to a misfolded disease protein/polypeptide that contains at least 80% of the contiguous amino acids of the full-length misfolded disease protein/polypeptide. However, it is also contemplated that a misfolded disease protein/polypeptides or heat shock protein containing at least about 85%, 90%, and 95% of SEQ ID NO:2, SEQ ID NO:4, SEQ ID NO:6, SEQ ID NO:8, or SEQ ID NO:9 are within the scope of the invention as a "substantially full-length" misfolded disease protein/polypeptide.

In various embodiments different lengths of the proteins/polypeptides of the present invention may be used. For example, only functionally active domains of the proteins may be used. Thus, a protein/polypeptide segment of almost any length may be employed.

In a non-limiting example, one or more proteins or polypeptides may be prepared that include a contiguous stretch of amino acids identical to or complementary to SEQ ID NO:2, SEQ ID NO:4, SEQ ID NO:6, SEQ ID NO:8, or SEQ ID NO:9. Such a stretch of amino acids, may be about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, about 500, about 510, about 520, about 530, about 540, about 550, about 560, about 570, about 580, about 590, about 600, about 610, about 620, about 630, about 640, about 650, about 660, about 670, about 680, about 690, to about 700 amino acids in length or longer, including all intermediate lengths and intermediate ranges. It will be readily understood that "intermediate lengths" and "intermediate ranges," as used herein, means any length or range including or between the given values (i.e., all integers including and between such values).

It is also contemplated that in the case of polyglutamine (pQ) containing polypeptide sequences the numeric order of the amino acids will not be changed by the number of the pQ repeats. In the example of a huntingtin's polypeptide encoded by Exon 1, the polypeptide is comprised of 68 amino acids, excluding pQ repeats. The pQ repeats typically begin at position 18. SEQ ID NO:9 is an example where there are no pQ repeats. However, in other examples variable number of pQ repeats are present, for example, SEQ ID NO:4 has 103 pQ repeats, and SEQ ID NO:6 has 25 pQ repeats. However, the numeric order of the amino acids 1-68 of Exon 1 will not be changed by the number of pQ repeats. Furthermore, these and other pQ comprising polypeptides of the invention are contemplated to have between 10 to 150 pQ repeats. This includes 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 1317, 13, 139, 140, 141, 142, 143, 144, 145, 146, 147, 148, 149, 150 pQ repeats.

F. Biological Functional Equivalents

One can also modify the sequence of any protein involved in fibril formation and/or in protein aggregation; or a heat shock protein; or a molecular chaperone protein, by amino-acid substitutions, replacements, insertions, deletions, truncations and other mutations to obtain fibril inhibitory and/or disassembling properties. These modification can generate functionally equivalent polypeptides may be obtained. The following is a discussion based upon changing of the amino acids of a protein or polypeptide to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties (see Table 4). It is thus contemplated by the inventors, that various changes may be made in the polypeptide sequences of the proteins involved in fibril formation and/or in protein aggregation; or a heat shock protein; or a molecular chaperone protein, with no change in the normal activity of the polypeptide.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

TABLE 4

Codon Table

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |
| Leucine | Leu | L | UUA | UUG | CUA | CUC | CUG | CUU |
| Methionine | Met | M | AUG | | | |
| Asparagine | Asn | N | AAC | AAU | | |

TABLE 4-continued

Codon Table

| Amino Acids | | | Codons | | | | | |
|---|---|---|---|---|---|---|---|---|
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

Another embodiment for the preparation of polypeptides or protein involved in fibril formation and/or in protein aggregation; or a heat shock protein; or a molecular chaperone protein, is the use of peptide mimetics. Mimetics are peptide-containing molecules that mimic elements of protein secondary structure. The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule.

G. Fusion Proteins

A fusion protein or chimeric protein is a specialized kind of protein variant that is an insertional variant. This molecule generally has all or a substantial portion of the native molecule, linked at the N- or C-terminus or in even at other parts of the protein, to all or a portion of a second polypeptide. In the present invention, fusion proteins have been generated that comprise regions/portions of the proteins involved in fibril formation and/or in protein aggregation; or a heat shock protein; or a molecular chaperone protein, that can be identified using either a fluorescence measuring method, a screening assay, or a functional assay. For example, fusions comprising a region of a alpha synuclein protein, a huntingtin protein, etc. linked to a green fluorescent protein (GFP) are described. Some of the GFP chimeras are N-terminal chimeras. Almost any type of fusion/chimeric protein may be prepared where the GFP region may be linked to other parts of the protein of interest. Other useful chimeras include linking of functional domains, such as active sites from enzymes, or epitopes that can be recognized by antibodies. These fusion proteins provide methods for rapid and easy detection and identification of the recombinant host cell, exemplified herein by the yeast cell.

H. Screening Methods of the Invention

The present invention provides methods for screening for candidate substances that prevent the misfolded protein disease and/or protein fibrillogenesis and/or the accumulation of protein deposits in tissues. In some embodiments these agents prevent protein misfolding. Irrespective of the exact mechanism of action, agents identified by the screening methods of the invention will provide therapeutic benefit to diseases involving protein misfolding or aberrant protein deposition. Some of these disorders are listed in Table 1 and include as non-limiting examples, neurodegenerative diseases such as, Huntington's, Parkinson's, Alzheimer's, prion-diseases, etc. as well as other non-neuronal diseases for example, type 2 diabetes.

The screening methods of the invention use yeast cells that are engineered to express proteins involved in fibril formation and/or in protein aggregation. The yeast cell also requires one of the two conditions described below for the screening method. In one module, the yeast cell have a mutant genetic background, for example, mutations in HSP genes or other molecular chaperone encoding genes, such as mutations in the HSP40 gene. Alternatively, the yeast cell expressing a protein involved in fibril formation and/or in protein aggregation can be subject to changes in growth conditions that lead to stress, such as oxidative stress, for example by exposing the cell to a free radical generator, or iron etc. Either of these conditions confers a toxic phenotype on the yeast cells expressing proteins involved in fibril formation and/or in protein aggregation. Contacting such a yeast cell with a candidate substance allows the identification of agents that can rescue the toxic phenotype of the yeast cell. The toxic phenotype is manifested as cytotoxicity or growth inhibition. The toxicity in yeast correlates to the cytotoxic effect of the protein in a human cell that causes the pathology associated with the disease caused by protein accumulation. For example, the expression of the huntingtin protein in a yeast cell, which additionally has a mutant HSP40 background, makes the yeast cell severely growth retarded. Contacting such yeast cells with candidate substances allows identification of agents that can reverse the growth retardation of yeast cells and hence the agent should also prevent the accumulation of huntingtin in a human cell. As huntingtin aggregation is involved in Huntington's disease, this screening method provides therapeutic agents to prevent and treat Huntington's disease.

(a) Candidate Substances

A "candidate substance" as used herein, is any substance with a potential to reduce, alleviate, prevent, or reverse the accumulation/aggregation of proteinaceous deposits in tissues. Various type of candidate substances may be screened by the methods of the invention. Genetic agents can be screened by contacting the yeast cell with a nucleic acid construct encoding for a gene. For example, one may screen cDNA libraries expressing a variety of genes, to identify therapeutic genes for the diseases described herein. In other examples one may contact the yeast cell with other proteins or polypeptides which may confer the therapeutic effect.

Thus, candidate substances that may be screened according to the methods of the invention include those encoding chaperone molecules, heat shock proteins, receptors, enzymes, ligands, regulatory factors, and structural proteins. Candidate substances also include nuclear proteins, cytoplasmic proteins, mitochondrial proteins, secreted proteins, plasmalemma-associated proteins, serum proteins, viral antigens, bacterial antigens, protozoal antigens and parasitic antigens. Candidate substances additionally comprise proteins, lipoproteins, glycoproteins, phosphoproteins and nucleic acids (for example, RNAs such as ribozymes or antisense nucleic acids). Proteins or polypeptides which can be screened using the methods of the present invention include chaperone proteins, hormones, growth factors, neurotransmitters, enzymes, clotting factors, apolipoproteins, receptors, drugs, oncogenes, tumor antigens, tumor suppressors, structural proteins, viral antigens, parasitic antigens and bacterial antigens. In addition, numerous methods are currently used for random and/or directed synthesis of peptide, and nucleic acid based compounds. The nucleic acid or protein sequences include the delivery of DNA expression constructs that encode them.

In addition, candidate substances can be screened from large libraries of synthetic or natural compounds. One example, is a FDA approved library of compounds that can be used by humans. In addition, synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.) and a rare chemical library is available from Aldrich (Milwaukee, Wis.). Combinatorial libraries are available and can be prepared. Alternatively, libraries of natural compounds in the form of bacterial, fungal, plant and animal extracts are also available, for example, Pan Laboratories (Bothell, Wash.) or MycoSearch (N.C.), or can be readily prepared by methods well known in the art. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds.

Other suitable modulators include antisense molecules, ribozymes, and antibodies (including single chain antibodies), each of which would be specific for the target molecule. Such compounds are described in greater detail elsewhere in this document. For example, an antisense molecule that bound to a translational or transcriptional start site, or splice junctions, would be ideal candidate inhibitors. Additionally, natural and synthetically produced libraries and compounds are readily modified through conventional chemical, physical, and biochemical means.

Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Useful compounds may be found within numerous chemical classes, though typically they are organic compounds, including small organic compounds. Small organic compounds have a molecular weight of more than 50 yet less than about 2,500 daltons, preferably less than about 750, more preferably less than about 350 daltons. Exemplary classes include heterocycles, peptides, saccharides, steroids, triterpenoid compounds, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g. for the amino group, acylation or alkylation, and for the carboxyl group, esterification or amidification, or the like.

(b) Screen with FRET and FACS

In one embodiment, the invention contemplates screening assays using fluorescent resonance energy transfer (FRET). In one example, alpha-synuclein is fused to cyan fluorescent protein (CFP) and to yellow fluorescent protein (YFP) and is integrated in the yeast genome under the regulation of a Gal1-10 promoter. Cells are grown in galactose to induce expression. Upon induction, cells produce the fusion proteins, which aggregate bringing the CFP and YFP close together. Because proteins in the aggregates are tightly packed, the distance between the CFP and YFP is less than the critical value of 100° A that is necessary for an energy transfer (FRET) to occur. In this case, the energy released by the emission of CFP will excite the YFP, which in turn will emit at its characteristic wavelength. The present inventors contemplate utilizing FRET bases screening to identify candidate compounds including, drugs, genes or other factors that can disrupt the interaction of CFP and YFP by maintaining the proteins in a state that does not allow aggregation to occur.

Cells will be sorted by fluorescence activated cell sorting (FACS) analysis, a technique well known to those of skill in the art. The inventors envision that this method of screening also enables the investigation of toxic intermediates formed in the aggregation pathway and will eventually allow a better understanding of how intermediates aggregate into insoluble proteins often characterized by plaques and tangles.

FACS, flow cytometry or flow microfluorometry provides the means of scanning individual cells for the presence of fluorescently labeled/tagged moiety. The method employs instrumentation that is capable of activating, and detecting the excitation emissions of labeled cells in a liquid medium. FACS is unique in its ability to provide a rapid, reliable, quantitative, and multiparameter analysis on either living or fixed cells. The misfolded disease proteins of the present invention, suitably labeled, provide a useful tool for the analysis and quantitation of protein aggregation and fibril and/or aggregate formation as a result of other genetic or growth conditions of individual yeast cells as described above.

(c) RNA Aptamers Screen

In another embodiment, the invention contemplates screening assays using RNA-aptamers. RNA is a nucleic acid capable of adopting a vast number of secondary structures, depending on its primary sequence. It is therefore possible to engineer RNA molecules with specific lengths so that they have the property of binding other molecules in a very specific manner and with very high affinity. This is similar to the phenomenon of antigen-antibody association.

The present inventors contemplate utilizing these properties of RNA molecules to identify RNA molecules that are candidate therapeutic agents for protein misfolding diseases, such as the neurodegenerative diseases. This is based on the ability of RNA molecules to recognize and bind misfolded disease proteins for example the amyloid fibers or other intermediate species in the pathway of aggregate/fibril formation.

The yeast-based screening system developed herein is amenable to such screens, and one may directly identify compounds that decrease the toxicity of misfolded disease proteins. In addition, one may identify compounds that disrupt the interaction between intermediates formed that lead to the aggregation of such proteins. It is also contemplated that one can screen for compounds that aggravate the toxicity or promote protein aggregation.

(d) Treatments

Initial testing and treatment of animal-models with test compounds identified by the screens of the invention are also contemplated. Suitable animal-model for the protein misfolding disease will be selected and treatment will involve the administration of the compound, in an appropriate pharmaceutical formulation, to the animal. Administration will be by any route that could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site. Determining the effectiveness of a compound in vivo may involve a variety of different criteria. Also, measuring toxicity and dose response can be performed in animals in a more meaningful fashion than in in vitro or in cyto assays.

I. Immunological Detection

It is also contemplated that one may detect the misfolded disease protein expression in the engineered yeast cells by immunological methods using suitable anti-misfolded disease protein antibodies. One can also use anti-heat shock protein antibodies or other anti-chaperone antibodies to detect the specific type of genetic mutation present in a yeast cell. The proteins, and/or polypeptides that can be detected include mutated versions.

In still further embodiments, the present invention thus concerns immunodetection methods for binding, purifying, removing, quantifying or otherwise generally detecting biological components. The steps of various useful immunodetection methods have been described in the scientific literature, such as, e.g., Nakamura et al. (1987; incorporated herein by reference). Immunoassays, in their most simple and direct sense, are binding assays. Certain preferred immunoassays are the various types of enzyme linked immunosorbent assays (ELISAs), radioimmunoassays (RIA) and immunobead capture assay. Immunohistochemical detection using tissue sections also is particularly useful. However, it will be readily appreciated that detection is not limited to such techniques, and Western blotting, dot blotting, FACS analyses, and the like also may be used in connection with the present invention.

In general, immunobinding methods include obtaining a yeast cell transformed with an expression construct expressing a protein or peptide and contacting the sample with an antibody to the protein or peptide in accordance with the present invention, as the case may be, under conditions effective to allow the formation of immunocomplexes.

The immunobinding methods of this invention include methods for detecting or quantifying the amount of a reactive component in a sample, which methods require the detection or quantitation of any immune complexes formed during the binding process. Here, one would obtain a yeast cell transformed with an expression construct expressing a protein or peptide of the invention and contact the sample with an antibody and then detect or quantify the amount of immune complexes formed under the specific conditions.

Contacting the chosen biological sample with the protein, peptide or antibody under conditions effective and for a period of time sufficient to allow the formation of immune complexes (primary immune complexes) is generally a matter of simply adding the composition to the sample and incubating the mixture for a period of time long enough for the antibodies to form immune complexes with, i.e., to bind to, any antigens present, such as antigens corresponding to misfolded disease proteins. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. Patents concerning the use of such labels include U.S. Pat. Nos. 3,817,837; 3,850, 752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The encoded protein, peptide or corresponding antibody employed in the detection may itself be linked to a detectable label, wherein one would then simply detect this label, thereby allowing the amount of the primary immune complexes in the composition to be determined.

Alternatively, the first added component that becomes bound within the primary immune complexes may be detected by means of a second binding ligand that has binding affinity for the encoded protein, peptide or corresponding antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the encoded protein, peptide or corresponding antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

J. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods for Ht Expression in Yeast

Plasmid Construction

Plasmids encoding fusions between GFP and the N-terminal region of Ht were the kind gift of the Hereditary Disease Foundation. To create yeast expression plasmids for HtQ25 or HtQ103 DNAs were digested with Xho I and Xba I, and the resulting Xho I/Xba I fragments were ligated into the vector pYES (Invitrogen) to obtain plasmids pYES/PQ25 or pYES/PQ103, respectively. These DNAs were digested with Sal I and ends were filled with Klenow enzyme. Afterwards DNAs were digested with EcoR I and the resulting fragments were subcloned into a high copy (211) expression vector p426 for constitutive expression or p426GAL for galactose induction, respectively (Mumberg et al., 1994; Mumberg et al., 1995).

To create low copy (CEN) expression plasmids with either constitutive (GPD) or galactose (GAL) inducible promotor DNAs, p426/PQ25 or p426/PQ103 were digested with Xho I. The resulting Xho I fragments were subcloned into p416 or p416GAL, respectively (Mumberg et al., 1994; Mumberg et al., 1995).

To generate the same set of yeast expression plasmids for HtQ47 or HtQ72 DNAs were double-digested with Acc 65I and Aba I, fragments were blunted with Klenow enzyme, and subcloned into a Cla I-blunted vector p426 for constitutive expression. To generate low copy expression plasmids with constitutive expression (GPD) DNA p426/PQ47 or p426/PQ72 were digested with Spe I and Xho I, and the resulting fragments were subcloned into p416.

The expression plasmids used in this study are listed in Table 5 (Kimura et al., 1995; Nathan et al., 1995; Vogel, et al., 1995).

TABLE 5

| Plasmid | Promoter | Copy Number | Reference |
|---|---|---|---|
| p416 | GPD | CEN, low | Mumberg, 1995 |
| p416/PQ25 | GPD | CEN, low | this study |
| p416/PQ47 | GPD | CEN, low | this study |
| p416/PQ72 | GPD | CEN, low | this study |
| p416/PQ103 | GPD | CEN, low | this study |
| p426 | GPD | 2μ, high | Mumberg, 1995 |
| p426/PQ25 | GPD | 2μ, high | this study |
| p426/PQ47 | GPD | 2μ, high | this study |
| p426/PQ72 | GPD | 2μ, high | this study |
| p426/PQ103 | GPD | 2μ, high | this study |
| p416GAL | GAL | CEN, low | Mumberg, 1994 |
| p416Gal/PQ25 | GAL | CEN, low | this study |
| p416Gal/PQ103 | GAL | CEN, low | this study |
| p426GAL | GAL | 2μ, high | Mumberg, 1994 |
| p426Gal/PQ25 | GAL | 2μ, high | this study |
| p426Gal/PQ103 | GAL | 2μ, high | this study |
| pTVSIS1 | GPD | 2μ, high | unpublished |
| pRSYDJ1 | GPD | CEN, low | Kimura et al., 1995 |
| pLH101 | GPD | 2μ, high | unpublished |
| pTGpd/P82 | GPD | CEN, low | Nathan & Lindquist, 1995 |
| p2HG(104) | GPD | 2μ, high | Vogel et al., 1995 |

Transformation of yeast was performed using a standard lithium/PEG method (Ito et al., 1983).

Yeast Strains, Transformation and Cultivation

In this study we used five isogenic series of yeast strains, in the backgrounds: W303 (MATa can1-100 ade2-1 his3-11, 15 trp1-1 ura3-1 leu2-3, 112), YPH499 (MATa ade2-101ochre his3-Δ200 leu2-Δ1 lys2-801amber trp-Δ63 ura3-52), MHY810 (MATa his3-Δ200 leu2-Δ1 lys1-1 met14 ura3-Δ1:: TRP1 trp1-Δ1), MHY501 (MATa his3-Δ200 leu2-3, 112 ura3-52 lys2-801 trp1-1) and MHY803 (MHY501 derivative: MATa his3-Δ200 leu2-3, 112 ura3-52 lys2-801 trp1-1 (doa3:: HIS3+) (Ycplac22-Doa3-His$_6$)). The MHY strains were kind gifts from Mark Hochstrasser. Yeast strains used are listed in Table 6.

TABLE 6

Aggregation of Mutant Huntingtin in Different Yeast Strains

| | | 2μ plasmids Aggregation of | | | | CEN plasmids Aggregation of | | | |
|---|---|---|---|---|---|---|---|---|---|
| | | Q25 | Q47 | Q72 | Q103 | Q25 | Q47 | Q72 | Q103 |
| | | Strain | | | | | | | |
| MHY810 | wild-type | − | −/+ | + | ++ | | | | |
| MHY898 | sen3-1 | − | −/+ | + | ++ | − | | + | ++ |
| MHY803 | wild-type | − | −/+ | + | ++ | | | | |
| MHY792 | doa3-1 | − | −/+ | + | ++ | − | | + | ++ |
| MHY501 | wild-type | − | −/+ | + | ++ | | | | |
| MHY1408 | uba1 | − | −/+ | + | ++ | | | | |
| YPH499 | wild-type | − | −/+ | + | ++ | | | | |
| DYJ1 | Δydj1 | − | −/+ | + | ++ | | | | |
| W303 | wild-type | − | −/+ | + | ++ | − | −/+ | + | ++ |
| LP6-2 | Δhsp26 | − | −/+ | + | ++ | | | | |
| LP8-1 | Δhsp35 | − | −/+ | + | ++ | | | | |
| SL314-A1 | Δssa1ssa2 | − | −/+ | + | ++ | | | + | ++ |
| SL318-2A | Δssa3ssa4 | − | −/+ | + | ++ | | | | |
| CLD82a | Δhsc82 | − | −/+ | + | ++ | | | + | ++ |
| iLEP1α | Δhsc82 | − | −/+ | + | ++ | | | | |
| SL304A | Δhsp104 | − | − | − | − | − | − | − | − |
| | | Overexpression | | | | | | | |
| wild-type | YDJ1 | | | | | | | + | ++ |
| wild-type | SIS1 | | | | | | | + | ++ |
| wild-type | SSA1 | | | | | | | + | + |
| wild-type | HSP82 | | | | | | | + | ++ |
| wild-type | HSP104 | | | | | | | + | + |
| Δhsp104 | YDJ1 | | | | | | | − | − |
| Δhsp104 | SIS1 | | | | | | | − | − |

Empty space no transformation made
− no foci fluorescence
−/+ a minority of cells have one small focus
+ one or more foci, with considerable background fluorescence
++ one or two intense fluorescence foci, with lower background fluorescence Transformation of yeast was performed using a standard lithium/PEG method (Ito et al., 1983).

Yeast cells were grown in rich media (YPD) or in minimal glucose/raffinose/galactose medium (Adams et al., 1997) deficient for the required amino acids for plasmid selection. For experimental purposes cells were grown overnight at 25° C. into log, late-log or early stationary phase.

Sedimentation Analysis

Yeast cells were harvested by centrifugation at 1500×g for 5 min at room temperature and washed once in 10 mM ethylenediaminetetraacetic acid (EDTA). Cells were resuspended in spheroplasting buffer (1 M sorbitol, 0.1 M EDTA, 0.5 mg/ml zymolyase 100T (Seikagaku Corporation), 50 mM dithiothreitol, pH 7.5) and incubated for 2 h at 30° C. Afterwards, spheroplasts were harvested by mild centrifugation at 325×g for 5 min at 4° C. and lysed in 1×TNE containing a protease-inhibitor cocktail (complete Mini-tablets, Boehringer Mannheim). After incubation in 1×TNE+2% Sarcosyl for 5 min on ice, samples were loaded onto a 5% (w/v) sucrose cushion (1 M sucrose, 100 mM NaCl, 0.5% sulfobetaine) and centrifugation was performed at 315,000×g for 1 hr at 4° C. Afterwards, supernatant and pellet fractions were subjected to 8% SDS-PAGE (Novex) and transferred to a polyvinylidene fluoride membrane (Millipore Corporation). Membranes were blocked with 5% nonfat-dehydrated milk powder in phosphate buffered saline (PBS) for 1 hr. Incubation with the primary antibody was performed overnight at 4° C. After incubation with Protein A-peroxidase (1:5000, Boehringer Mannheim), the immune complexes were visualized by treating membranes with ECL reagent (Amersham). Antibody αGFP was used at 1:100 (Clontech).

Microscopy

Yeast cells were allowed to adhere onto polylysine-treated slides for 10 min. For nucleus staining, cells were fixed with 1% formaldehyde for 5 min and washed 3 times with PBS. After treatment with 4',6-diamidine-2-phenylindole-dihydrochloride (DAPI, Sigma) for 5 min, cells were washed 3 times with PBS. Microscopy was performed with a Axioplan 2 microscope (Zeiss), and micrographs were taken at a magnification of 100×.

Example 2

Coalescence of Mutant Ht in Yeast

To investigate Ht in yeast, the N-terminal region (amino acids 1-68 of the wild-type protein) with a wild-type polyQ (polyglutamine) repeat length of 25 residues or with mutant repeat lengths of 47, 72 or 103 residues was fused to GFP. Each was placed under the control of GPD, a strong constitutive yeast promoter, on a single copy plasmid (FIG. 1). Homopolymeric tracts of CAG, the naturally occurring glutamine codon in Ht, are inherently unstable, and particularly so in yeast (Moore et al., 1999; Schweitzer et al., 1997). This problem was reduced by the fact that glutamine is encoded by both CAG and CAA and that mixed codon repeats are considerably more stable (Kazantsev et al., 1999). To minimize instability problems, all experiments reported herein were performed with mixed codon polyQ repeats and all work was performed with fresh transformants, using at least two independent colonies in each case, and repeated at least two times.

Fluorescence from GFP-fusion proteins containing wild-type polyglutamine tracts (25 residues; HtQ25) was always distributed diffusely throughout the cell (FIG. 1, middle). HtQ47 fluorescence was also diffusely distributed, although coalescent foci were observed in a small percentage of cells (less than 2%). More than half of cells expressing HtQ72 exhibited a single intense spot of fluorescence against a diffuse fluorescent background. Virtually all cells expressing HtQ103 exhibited a single intense spot of fluorescence, with much less background fluorescence than seen with other variants. When the same constructs were expressed from high-copy plasmids (p426 series, Table 5), fluorescence intensity was much greater, but the pattern of fluorescence was very similar. Immunoblotting of total cellular protein indicated that all four variants were expressed at similar levels. Thus, the degree of coalescence exhibited by the N-terminal fragment of Ht depends more upon the length of the polyglutamine tract than the level of protein expressed.

Example 3

Newly Induced Mutant Ht Aggregates in all Cells

Cells expressing different Q repeat variants exhibited the same frequency of plasmid loss (determined by plating cells to non-selective and selective media) and grew at similar rates, with only a slight deficit in cells expressing HtQ103. Final densities were typically 0.7-0.8 for cells expressing HtQ25, HtQ47 or HtQ72 and 0.5-0.7 for cells expressing HtQ103. Thus, the long polyQ Ht fragments were not overtly toxic in yeast. However, because the proteins were expressed from a constitutive promoter, it was possible that a subset of cells competent to grow in the presence of polyQ proteins had been selected during transformation. If so, selection might also have influenced the aggregation state of the proteins. To determine if the coalescence of expanded glutamine reflected an inherent property of the protein or was the result of a selective process, the Ht-GFP constructs were transferred to the control of a galactose-inducible promoter (Table 5). Transformants were selected on glucose plates to keep the construct tightly repressed. To initiate induction, cells were first grown in raffinose medium overnight, to eliminate glucose repression, and then transferred to galactose medium, to induce Ht expression.

Bright GFP fluorescence was observed after 4 hours, but for all three variants tested, HtQ25, HtQ72, and HtQ103, fluorescence was diffusely distributed. With continued expression HtQ72 and HtQ103 coalescence began to appear in some cells after 9 hrs (2 doublings). After 24 hrs, coalescence was indistinguishable from that observed in cultures expressing the Ht variants constitutively and all cultures had reached similar densities. Thus, coalescence of expanded glutamine repeats occurs in most, if not all, cells in the culture, but many hours of expression are required for it to occur.

Example 4

Mutant Ht Forms Cytoplasmic Aggregates in Yeast

Co-staining cells with DAPI, a DNA-binding dye that fluoresces blue, demonstrated that foci of Ht coalescence were in the cytoplasmic compartment not in the nucleus. To determine if these foci reflected the sequestration of Ht-GFP fusions into a membrane-bounded compartment or the formation of higher order protein complexes, cell walls were removed and cells were lysed in the presence of the detergent Sarkosyl (2%). After sedimentation, supernatant and pellet fractions were boiled in sample buffer containing 5% SDS for 10 minutes and analyzed by immunoblotting.

HtQ25 and HtQ47 were detected only in supernatant fractions. HtQ72 was distributed between supernatant and pellet fractions, whereas virtually all HtQ103 protein was found in the pellet fraction. Note that after electrophoresis a major fraction of HtQ103 remained at the top of the gel. Apparently, the coalescence detected through GFP fluorescence was due to the formation of higher order complexes. For HtQ103, and less so for HtQ72, these complexes resisted solubilization by boiling in 5% SDS.

Example 5

Aggregates are Unaltered in Proteasome-Deficient Cells

Because aggregates of Ht (Saudou et al., 1998) and other glutamine-repeat proteins associated with disease, such as SBMA (Stenoien et al., 1999), SCA3 (Chai et al., 1999) and SCA1 Cummings et al., 1998), are ubiquitinated in mammalian cells and are associated with components of the proteosome, it has been suggested that the ubiquitin/proteosome pathway might be involved in aggregate formation. Ubiquitinated Ht proteins were not detected in yeast cells. However, even for proteins known to be turned over by this pathway ubiquitin conjugates can be difficult to detect. To investigate this question more rigorously, a genetic approach was undertaken. Three strains were employed, each containing a lesion in a different component of the ubiquitin/proteasome degradation pathway: 1) uba1, the ubiquitin activating enzyme (M. Hochstrasser), 2) doa3, a catalytic subunit of the 20S proteasome (Chen et al., 1995), and 3) sen3 a subunit of the 19S proteasome regulatory complex (DeMarini et al., 1995). Since each of these genes is essential, partial loss-of-function mutations were used that severely impair this pathway. In each of the strains, the Ht variants behaved in the same manner as they did in wild-type cells. There were no changes in the number of cells containing coalescent foci, nor in the size or intracellular distribution of those foci (Table 6).

Example 6

Molecular Chaperones Affect Aggregation of Ht

Chaperone proteins are a highly conserved, but diverse group of proteins that control the folding of other proteins by interacting with different types of folding intermediates and off pathway folding products (Gething, 1997). They have profound effects on the aggregation of abnormal proteins. To determine how changes in the levels of chaperone proteins would affect the coalescence of the Ht polyQ variants, an isogenic series of strains was generated containing deletion mutations or over-expression plasmids for various chaperone proteins, which produced wild-type or polyQ expanded Ht fragments. Note that some chaperone deletions could not be tested because they are lethal.

Most of the tested alterations in chaperone proteins had no noticeable effects on the intracellular distribution of Ht variants as determined by GFP fluorescence (Table 6) and no significant effect on the manner in which the Ht fragments were partitioned between the supernatant and pellet fractions after sedimentation. This category included mutations that eliminated the expression of the major small Hsp (in yeast, Hsp26) (Petko et al., 1986), 2) increased the expression of Hsp90 (in yeast, Hsc/p82) several fold (Borkovich et al., 1989) or reduced the expression of Hsp90 by 10- to 15-fold (Nathan et al., 1999), 3) eliminated the expression of various members of the essential cytosolic Hsp70 family (constitutive members Ssa1 and Ssa2 (Parsell et al., 1994a and b), and stress inducible members Ssa3 and Ssa4, and 4) increased or eliminated expression of Ydj1 (a member of the Hsp40 family) (Kimura et al., 1995). A deletion of Hsp35 was also examined. This heat-inducible protein is a member of the glyeraldehyde-3-phosphate dehydrogenase family and is postulated to be a chaperone because it is both heat inducible and one of the most abundant proteins in yeast (Boucherie et al., 1995). Mammalian glyeraldehyde-3-phosphate dehydrogenase exhibits a glutamine length-dependent association with Ht (Burke et al., 1996).

Over-expression of three chaperones had significant effects. Sis1, a member of the Hsp40 family, caused two intense foci of aggregation to appear in most cells with HtQ72 and HtQ103, rather than the single focus of coalescence observed in virtually all wild-type cells. In cells over-expressing Hsp70 (Ssa1), HtQ72 and HtQ103 fluorescence was much more variable than in wild-type cells. Multiple foci of fluorescence were observed in many cells, and many also contained a higher background of diffuse fluorescence. This variability likely reflects differences in plasmid copy number, which is commonly observed with Hsp70 expression plasmids (Stone et al., 1990). Over-expression of Hsp104 also increased the number of fluorescent foci and the background fluorescence observed with the Ht variants HtQ72 and HtQ103 (Table 6). It also increased the relative quantities of HtQ72 and HtQ103 found in the supernatant fractions after centrifugation. Curiously, although HtQ72 protein appeared at least partially aggregated in these cells, little protein fractionated in the pellet in three out of three experiments. The protein may be more loosely packed or in a Sarkosyl-soluble state.

Of all the chaperone alterations tested, a deletion of the HSP104 gene had the most dramatic effect. In these strains, all of the Ht variant fragments exhibited diffuse fluorescence. The same results were obtained with both the high and low copy Ht expression constructs (Table 6). Moreover, by sedimentation, all of the proteins were only detected in supernatant fractions.

Example 7

Hsp40 Alters Aggregation of Ht Variants

That Sis1 (a class II yeast Hsp40 protein) affected the aggregation state of huntingtin and that Hsp40 proteins, most particularly HDJ-1, seem to play a crucial role in polyQ-induced toxicity in several model systems led to a more detailed analysis of Sis1. Yeast strains engineered to express different regions of the Sis1 protein were transformed with the huntingtin-GFP fusion constructs described in the above Examples. The aggregation pattern of HtQ72 and HtQ103 was markedly altered by the production of mutant Sis1 proteins. Instead of a small number of large aggregates, a large number of smaller aggregates were present. Most notably, with one Sis1 construct this change in aggregation was accompanied by a reduction in viability. This Sis1-induced toxicity can be reduced by co-expression of Hsp104. Hsp104 also reduces both aggregate formation and cell death in a mammalian cell model of huntingtin toxicity and in a *C. elegans* model employing simple polyQ-GFP-fusions. These striking observations suggest that the toxicity of huntingtin induced by Sis1 alterations in yeast can be considered directly related to its toxicity in humans.

Example 8

Compounds that Affect Huntingtin Toxicity in Yeast

Using the strain expressing the truncated Sis1 protein and HtQ103 (toxic), screens were performed using the spotting assays described in Examples 9 and 10 below. Further screens with other candidate agents are also contemplated. These screens allow identification of agents that affect huntingtin aggregation in the living cell but are by themselves non-toxic.

Specifically, yeast strains in the mutant Sis1 background expressing HtQ25 (control, not toxic), or HtQ72 (not toxic, but potentially so), or HtQ103 (toxic) were spotted in serial dilutions onto selective media with or without test compounds. HtQ47 will also be spotted in serial dilutions onto selective media with or without test compounds in similar experiments. Increased growth rate on test plates compared to control plates identifies compounds with a potential for reducing toxicity; a decreased growth identifies compounds that might increase toxicity. Microscopic analysis determines whether these agents also affect aggregate formation by the GFP-fusion proteins. This screen will also be performed with yeast strains expressing only the N-terminal region of huntingtin, not fused to GFP.

Spotting assays demonstrate that various compounds, including several listed in Table 3, induce toxicity in the yeast strains which comprise W303, hsp104, and Sis1 mutants.

One concern in yeast screens is that some agents may not be able to enter the yeast cell, can not be taken up, are rapidly metabolized, or pumped out of the cell. To eliminate this possibility a variant of yeast strains designed to eliminate this problem will be employed. A strain mutant in 3 genes (erg6, pdr1, and pdr3) affecting membrane efflux pumps (Cummings et al., 1998) and increasing permeability for drugs (Chen et al., 1995) will be used in initial studies. These particular strains has been used very successfully in cancer research to identify growth regulators (see Website: http://dtp.nci.nih.gov).

Example 9

Materials and Methods for Toxicity in Yeast Expressing Misfolded Disease Proteins Plasmid Constructions Wild-type (WT), A53T and A30P alpha-synuclein cDNAs were a kind gift from Dr. Peter Lansbury. WT, A53T, and A30P sequences were subcloned into p426GPD, p416GPD, p423GPD and p425GPD (Mumberg et al., 1995) by standard molecular biology procedures. GFP, CFP and YFP fusions which are fusions of alpha-synuclein in frame with GFP, CFP or YFP were constructed by inserting the XFP (X meaning G, C or Y) coding sequence in frame with alpha-synuclein in the same vectors. The XFP fusions were also subcloned into pRS306 and pRS304 under the regulation of a GAL1-10 promoter and with a Cyc1 terminator region.

Yeast Techniques

Yeast strains were grown and manipulated following standard procedures (see Guthrie and Fink, Guide to Yeast Genetics and Molecular Biology, Academic Press, 1991).

Spotting Experiments

Yeast cells were routinely grown overnight at 30° C. or at room temperature in selective media until they reached log or late log phase. Cells were counted using a hemocytometer and diluted to $1 \times 10^6$ cells/ml. Five serial dilutions (five-fold) were made and cells were spotted onto media containing chemicals/drugs to screen.

Example 10

Alpha-Synuclein Forms Fluorescent Foci in the Yeast Cytoplasm

Using GFP fusions the formation of fluorescent foci dispersed throughout the cytoplasm were detected. These inclusions were more prominent with the WT and A53T mutant than with the A30P. Using this kind of assay the formation of inclusions by A30P cannot be ruled out, but a different kind of aggregates has to be expected in this case, as the GFP fluorescence pattern looks different.

Example 11

Conditions Increasing the Toxicity of Alpha-Synuclein

Using spotting experiments different categories of chemicals were identified as agents capable of aggravating the toxicity of alpha-synuclein overexpression or of inducing toxicity of huntingtin expression. Of the compounds tested in Table 3, the following had a negative effect on the growth of yeast cells overexpressing WT alpha-synuclein: carbon sources (arabinose 2%); nitrogen sources (urea 1 mg/ml); salts and metals ($CaCl_2$ 0.5 M, $CoCl_2$ 750 µM, CsCl 0.1 M, $CuSo_4$ 2.5 mM, $CuSo_4$ 5 mM, $Fe_2(SO_4)_3$ 8.5 mM, $FeSO_4$ 20 mM, $FeCl_2$ 10 mM, $FeCl_2$ 15 mM, $FeCl_2$ 23 mM, $FeCl_2$ 50 mM, $MgCl_2$ 0.5 M, $MgSO_4$ 0.5 M, RbCl 0.2 M, $SrCl_2$ 0.5 M); and, general inhibitors (6-azauracil 30 µg/ml, aurintricarboxylic acid 100 µM, bleomycin 1 µg/ml, brefeldin A 100 µg/ml, camptothecin 5 µg/ml, chlorambucil 3 mM, ethidium bromide 50 µg/ml, formamide 2%, GuHCl 20, hydroxyurea 5 mg/ml, menadione 20-50 µM, paraquat 1 mM (methyl viogen), vanadate 1 mM, vanadate 0.1 mM, vanadate 2 mM, vanadate 4 mM, vanadate 7 mM+KCl.

Some compounds, in a preliminary study, exhibited an ability to alleviate toxocity caused by alpha-synuclein overexpression. These included: nitrogen source (serine 1 mg/ml); general inhibitors (camptothecin 0.1 µg/ml, DL-C-allylglycine 0.025 mg/ml, Hygromycin B 50 µg/ml, L-ethionine 1 µg/ml, paromomycin 200 µg/ml, protamine sulphate 250 µM); vitamins (B12); proteasome inhibitors (chloroquine 4.2 µM, clioquinol 5 µM, (R)-(−)-3-hydroxybutirate, L-DOPA); amyloid-related compounds (Congo Red 5 µM, chrysamine G 1.0 µM, Deoxycorticosterone); and, anti-oxidants (glutathione).

Example 12

Screen with FRET and FACS

Figure 4:
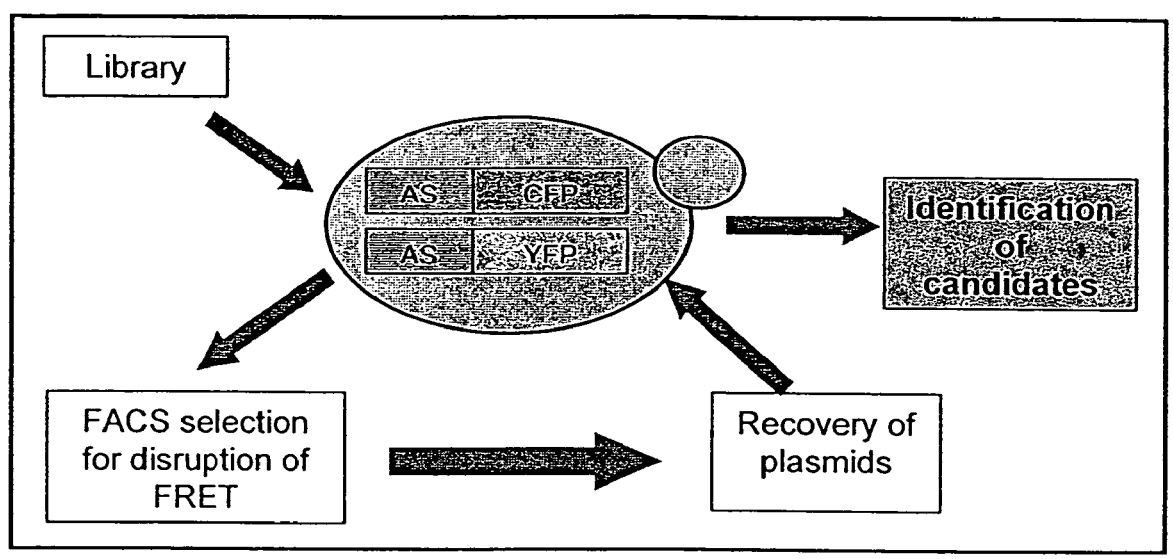
FIG. 4. Schematic of the screen of a DNA library based on the disruption of FRET between the proteins tagged with CFP and YFP.

Alpha-synuclein fused to CFP and to YFP was integrated in the yeast genome under the regulation of a Gal1-10 promoter (FIG. 4). Cells are grown in galactose to induce expression. Upon induction, cells will produce the fusion proteins, which will aggregate bringing the CFP and YFP close together. Because the proteins in the aggregates are tightly packed, the distance between the CFP and YFP will be less than the critical value of 100 Å that is necessary for an energy transfer (FRET) to occur. In this case, the energy released by the emission of CFP will excite the YFP, which in turn will emit at its characteristic wavelength. Thus, this phenomenon can be used to identify drugs, genes or other factors that may disrupt this interaction by maintaining the proteins in a state that does not allow for aggregation to occur. These factors will be analyzed by sorting cells by FACS analysis. This allows the investigation of toxic intermediates in the aggregation pathway and thus addresses whether the aggregates or other intermediates are causing cell death.

Example 13

RNA Aptamers Screen

RNA aptamers will be screen to identify ones that would have potential applications as therapeutics for neurodegenerative diseases due to their ability to recognize and bind amyloid fibers or other intermediate species in the pathway. The yeast system would thus be very amenable for doing this screens, either by looking directly for molecules that would decrease the toxicity of alpha-synuclein overexpression as well as by looking for molecules that would disrupt the interaction between the species that lead to aggregation of the protein. Also interesting would be to find some molecules that would aggravate the toxicity or promote the aggregation, as this could give insight into the epitopes necessary for fibrillogenesis/aggregation of this and other proteins implicated in human disease.

All of the COMPOSITIONS and/or METHODS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS and/or METHODS and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

EP 266,032
U.S. Pat. No. 3,817,837,
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,554,101
U.S. Pat. No. 4,682,195
U.S. Pat. No. 4,683,202
U.S. Pat. No. 5,643,562
U.S. Pat. No. 5,645,897
U.S. Pat. No. 5,705,629
U.S. Pat. No. 5,928,906
Adams et al., Cold Spring Harbor Laboratory Press, 1997.
Almendro et al., *J Immunol.*, 157:5411-5421, 1996.
Ausubel et al., Yeast Cloning Vectors and Genes, Current Protocols in Molecular Biology, Section II, Unit 13.4, Eds., 1994.
Bao et al., *Proc Natl Acad Sci USA.* 93:5037-42, 1996.
Borkovich et al., *Mol Cell Biol.* 9:3919-30, 1989.
Boucherie et al., *FEMS Microbiol Lett.* 125:127-33, 1995.
Boutell et al., *Hum Mol Genet.* 7:371-8, 1998.
Burke et al., *Nat Med.* 2:347-50, 1996.
Carbonelli et al., *FEMS Microbiol Lett*, 177(1):75-82, 1999.
Chai et al., *J Neurosci.* 19:10338-47, 1999.
Chai et al., *Hum Mol Genet.* 8:673-82, 1999.
Chandler et al., *Proc Natl Acad Sci USA.* 94(8):3596-3601, 1997.
Cheetham et al., *Cell Stress Chaperones.* 3:28-36, 1998.
Chen et al., *Embo J.* 14:2620-30, 1995.
Chernoff et al., *Science.* 268:880-4, 1995.
Cocea, *Biotechniques,* 23(5):814-816, 1997.
Cummings et al., *Nat Genet.* 19:148-54, 1998.
Davies et al., *Lancet.* 351:131-3, 1998.
Davies et al., *Cell.* 90:537-48, 1997.
DeMarini et al., *Mol Cell Biol.* 15:6311-21, 1995.
DiFiglia et al., *Science.* 277:1990-3, 1997.
Editorial article, *Amyloid: Int. J. Exp. Clin. Invest.* 6, 63-66, 1999.
Editorial article, *Amyloid: Int. J. Exp. Clin. Invest.* 6, 67-70, 1999.
Froehler et al., *Nucleic Acids Res.* 14(13):5399-5407, 1986.
Gao et al., *Biotechniques,* 29:1226-1231, 2000.
Gething, M. J., Guidebook to molecular chaperones and protein folding catalysts. Oxford University Press, 1997.
Gietz et al., Gene, 74:527-534, 1988.
Grant et al., Methods Enzymol. 153:516-544, 1987.
Gusella et al., *Mol Med.* 3:238-46, 1997.
Guthrie and Fink, Eds. Guide to Yeast Genetics and Molecular Biology, San Diego: Academic Press, 1991.
Huntington's Disease Collaborative Research Group, *Cell.* 72:971-83, 1993.
Ito et al., *J Bacteriol.* 153:163-8, 1983.
Jana et al., *Hum Mol Genet.* 9(13):2009-18, 2000.
Kazantsev et al., *Proc Natl Acad Sci USA.* 96:11404-9, 1999.
Kimura et al., *Science.* 268:1362-5, 1995.
Kraus et al. *FEBS Lett.,* 428(3):165-170, 1998.
Krobitsch et al., *Proc Natl Acad Sci USA.* 97(4):1589-94, 2000.
Kushnirov et al., *Cell.* 94:13-6, 1998.
Kyte and Doolittle, *J. Mol. Biol.,* 157:105-132, 1982.
Lareyre et al., *J Biol. Chem.,* 274(12):8282-8290, 1999.
Lee et al., *J Auton Nerv Syst.* 74(2-3):86-90, 1997.
Levenson et al., *Hum Gene Ther,* 9(8):1233-6, 1998.
Li et al., *J Biol. Chem.* 273:19220-7, 1998.
Macejak and Sarnow, *Nature,* 353:90-94, 1991.
Mangiarini et al., *Cell.* 87:493-506, 1996.
Martin et al., *N Engl J. Med.* 315:1267-76, 1986.
Martindale et al., *Nat Genet.* 18:150-4, 1998.
Moore et al., *Proc Natl Acad Sci USA.* 96:1504-9, 1999.
Mumberg et al., Gene, 156(1):119-22, 1995.
Mumberg et al., *Nucleic Acids Res.* 22:5767-8, 1994.
Mumberg et al., *Gene.* 156:119-22, 1995.
Nakamura et al., *In: Handbook of Experimental Immunology* (4th Ed.), Weir, Herzenberg, Blackwell, Herzenberg, (eds). Vol. 1, Chapter 27, Blackwell Scientific Publ., Oxford, 1987.
Nathan et al., *Mol Cell Biol.* 15:3917-25, 1995.
Nathan et al., *Proc Natl Acad Sci USA.* 96:1409-14, 1999.
Nomoto et al., *Gene,* 236(2):259-271, 1999.
Ordway et al., *Cell.* 91:753-63, 1997.
Parsell et al., *Annu Rev Genet.* 27:437-96, 1993.
Parsell et al., *Nature.* 372:475-8, 1994(a).
Parsell et al., *J. Biol. Chem.* 269(6):4480-7, 1994(b).
Patino et al., *Science.* 273:622-6, 1996.
Pelletier and Sonenberg, *Nature,* 334:320-325, 1988.
Perutz, *Trends Biochem Sci.* 24:58-63, 1999.
Petko et al., *Cell.* 45:885-94, 1986.
Picard et al., *Gene,* 86:257-261, 1990.
Reddy et al., *Trends Neurosci.* 22:248-55, 1999.
Reddy et al., *Curr. Opin Cell Biol.* 9:364-72, 1997.
Ronicke et al., *Methods in Enzymol.,* 283:313-322, 1997.
Rose et al., Methods in Yeast Genetics, Cold Spring Harbor Laboratory Press, Cold Spring Harbor, N.Y., 1990.
Ross, *Neuron.* 19:1147-50, 1997.
Satyal et al., *Proc. Acad. Sci. USA* 97(11):5750-5, 2000.

Sambrook et al., In: *Molecular Cloning: A Laboratory Manual*, 2nd Ed., Cold Spring Harbor Press, Cold Spring Harbor, N.Y., 1989.
Saudou et al., *Cell*. 95:55-66, 1998.
Scherzinger et al., *Cell*. 90:549-58, 1997.
Schweitzer et al., *Hum Mol Genet*. 6:349-55, 1997.
Sikorski, "Extrachromsomoal cloning vectors of *Saccharomyces cerevisiae*", in Plasmid, A Practical Approach, Ed. K. G. Hardy, IRL Press, 1993.
Stenoien et al., *Hum Mol Genet*. 8:731-41, 1999.
Stone et al., *Mol Cell Biol*. 10:1622-32, 1990.
Tsumaki et al., *J Biol. Chem*. 273(36):22861-22864, 1998.
Vogel et al., *J Neuropathol Exp Neurol*. 44:559-77, 1995.
Warrick et al., *Nat Genet*. 23:425-428, 1999.
Wu et al., *Biochem Biophys Res Commun.*, 233(1):221-226, 1997.
Zhao-Emonet et al., *Biochem. Biophys. Acta.*, 1442(2-3):109-19, 1998.
Zoghbi et al., *Curr Opin Neurobiol*. 9:566-570, 1999.

What is claimed is:

1. A method of screening for a compound that decreases huntingtin associated toxicity, the method comprising:
   providing a yeast cell engineered to express a protein comprising a huntingtin polypeptide;
   contacting the yeast cell with a candidate compound; and
   evaluating the yeast cell for viability, wherein an increase in viability of the yeast cell as compared to viability of the yeast cell in the absence of the candidate compound indicates that the candidate compound decreases huntingtin associated toxicity.

2. The method of claim 1, wherein the yeast cell has a genetic background that causes the yeast cell to have a reduced growth rate or no growth at all as a result of expressing the protein comprising a huntingtin polypeptide.

3. The method of claim 2, wherein the yeast cell does not express wild-type Hsp40.

4. The method of claim 1, wherein the protein is a fusion protein.

5. The method of claim 4, wherein the fusion protein comprises a reporter polypeptide.

6. The method of claim 5, wherein the reporter polypeptide is green fluorescent protein.

7. The method of claim 5, wherein the reporter polypeptide is Sup35.

8. The method of claim 3, wherein the yeast cell expresses a truncated Hsp40 polypeptide.

9. The method of claim 8, wherein the Hsp40 polypeptide has a C-terminal deletion.

10. The method of claim 9, wherein the C-terminal deletion comprises amino acids 173-352 of SEQ ID NO:8.

11. The method of claim 9, wherein the C terminal deletion comprises amino acids 122-352 of SEQ ID NO:8.

12. The method of claim 1, wherein the candidate compound is a small organic compound having a molecular weight of more than 50 daltons and less than 350 daltons or a nucleic acid.

13. A method of screening for a compound that decreases huntingtin associated toxicity, the method comprising:
   contacting a yeast cell with a candidate compound, wherein the yeast cell expresses a polypeptide comprising a huntingtin polypeptide;
   contacting the yeast cell with a toxicity inducing agent; and
   evaluating the yeast cell for viability, wherein an increase in viability of the yeast cell as compared to viability of the yeast cell in the absence of the candidate compound indicates that the candidate compound decreases huntingtin associated toxicity.

14. The method of claim 13, wherein the toxicity inducing agent is a liposome, antibiotic, anisomycin, bleomycin, caffeine, camptothecin, carbonyl-cyanide, daunomycin, ethanol, formamide, GuHCL, or NEM.

15. The method of claim 13, wherein the toxicity inducing agent is arabinose.

16. The method of claim 13, wherein the toxicity inducing agent is potassium acetate.

17. The method of claim 13, wherein the toxicity inducing agent is a salt or metal.

18. The method of claim 17, wherein the salt or metal is $CdCl_2$, $CoCl_2$, $CsCl$, $FeCl_2$, $LiCl$, $NH_4Cl$, $RbCl$, or $ZnCl_2$.

19. The method of claim 13, wherein the candidate compound is a small organic compound having a molecular weight of more than 50 daltons and less than 350 daltons or a nucleic acid.

* * * * *

UNITED STATES PATENT AND TRADEMARK OFFICE
CERTIFICATE OF CORRECTION

| | | |
|---|---|---|
| PATENT NO. | : 8,039,209 B2 | |
| APPLICATION NO. | : 11/363870 | |
| DATED | : October 18, 2011 | |
| INVENTOR(S) | : Lindquist et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1054 days.

Signed and Sealed this
Twentieth Day of March, 2012

David J. Kappos
*Director of the United States Patent and Trademark Office*